US012758409B2

(12) United States Patent
Barbarino et al.

(10) Patent No.: US 12,758,409 B2
(45) Date of Patent: Oct. 13, 2026

(54) COSMETIC SECUREMENT DEVICE FOR STABILIZATION OF COSMETIC APPLICATOR CONFIGURED FOR USERS WITH LIMITED MOBILITY

(71) Applicant: L'OREAL, Paris (FR)

(72) Inventors: Casey Barbarino, San Anselmo, CA (US); Hyosik Dennis Min, Palisades Park, NJ (US)

(73) Assignee: L'OREAL, Paris (FR)

( * ) Notice: Subject to any disclaimer, the term of this patent is extended or adjusted under 35 U.S.C. 154(b) by 631 days.

(21) Appl. No.: 18/362,423

(22) Filed: Jul. 31, 2023

(65) Prior Publication Data

US 2025/0040833 A1 Feb. 6, 2025

(51) Int. Cl.

*A61F 4/00* (2006.01)
*A45D 40/26* (2006.01)
*A45D 44/00* (2006.01)
*A61B 5/11* (2006.01)

(52) U.S. Cl.

CPC .............. *A61F 4/00* (2013.01); *A45D 40/265* (2013.01); *A45D 44/00* (2013.01); *A45D 2200/10* (2013.01); *A61B 5/1101* (2013.01); *A61B 2562/0219* (2013.01)

(58) Field of Classification Search

CPC ........................................................ A61F 4/00
See application file for complete search history.

(56) References Cited

U.S. PATENT DOCUMENTS

| | | | | |
|---|---|---|---|---|
| 8,308,664 | B2 * | 11/2012 | Pathak | A47G 21/02 600/595 |
| 9,925,034 | B2 * | 3/2018 | Pathak | A61F 4/00 |
| 9,943,430 | B2 * | 4/2018 | Pathak | A61F 4/00 |
| 10,058,445 | B2 * | 8/2018 | Pathak | A61B 34/75 |
| 10,070,807 | B2 * | 9/2018 | Shoeb | G16H 50/20 |
| 10,159,428 | B1 * | 12/2018 | Shoeb | A61B 5/4082 |

(Continued)

OTHER PUBLICATIONS

Preliminary Search Report and Written Opinion issued May 21, 2024, in corresponding French Patent Application No. 2311345 (with English translation of Category of Cited Documents).

(Continued)

*Primary Examiner* — Angela M Hoffa
(74) *Attorney, Agent, or Firm* — Womble Bond Dickinson (US) LLP

(57) ABSTRACT

Provided here is a cosmetic securement device for stabilization of a cosmetic applicator. In an embodiment, the cosmetic securement device may include a motion stabilizer handle. The cosmetic securement device may include an internal sleeve configured to be removably inserted into the motion stabilizer handle. The cosmetic securement device may include an adapter coupled to a first end of the cosmetic securement device. In embodiments, the internal sleeve may include a positioning joint at a first end of the internal sleeve, the first end of the internal sleeve may align with a first end of the motion stabilizer handle when the internal sleeve is inserted into the motion stabilizer handle. The motion stabilizer handle may include at least one releasable locking mechanism configured to secure the internal sleeve inside the motion stabilizer handle, and wherein the adapter is configured to hold a plurality of different types of cosmetic applicators.

19 Claims, 24 Drawing Sheets

(56) References Cited

U.S. PATENT DOCUMENTS

| | | | | |
|---|---|---|---|---|
| 10,159,432 | B1 * | 12/2018 | Pathak | G01C 19/00 |
| 10,219,930 | B2 * | 3/2019 | Pathak | G05B 13/021 |
| 10,264,904 | B1 * | 4/2019 | Kim | A47G 21/08 |
| 10,271,770 | B2 * | 4/2019 | Pathak | A61B 5/1126 |
| 10,368,669 | B2 * | 8/2019 | Pathak | G16H 40/67 |
| 10,420,663 | B2 * | 9/2019 | Pathak | A61F 4/00 |
| 10,455,963 | B2 * | 10/2019 | Pathak | A47G 21/02 |
| 10,532,465 | B2 * | 1/2020 | Pathak | A61F 4/00 |
| 10,583,061 | B2 * | 3/2020 | Pathak | G05B 15/02 |
| 10,600,596 | B2 * | 3/2020 | Pathak | F16B 21/065 |
| 10,758,388 | B2 * | 9/2020 | Pathak | A61B 5/486 |
| 10,851,867 | B2 * | 12/2020 | Pathak | A47G 21/04 |
| 11,058,598 | B2 * | 7/2021 | Pathak | A61B 5/1101 |
| 11,369,500 | B2 * | 6/2022 | Pathak | A61B 5/1114 |
| 11,883,342 | B2 * | 1/2024 | Pathak | A47G 21/02 |
| 11,944,216 | B2 * | 4/2024 | Pathak | A47G 21/02 |
| 11,980,305 | B1 * | 5/2024 | Wagoner | F16F 7/04 |
| 12,133,591 | B2 * | 11/2024 | Lee | F16B 21/02 |
| 12,396,544 | B2 * | 8/2025 | Barbarino | A45F 3/00 |
| 12,490,823 | B2 * | 12/2025 | Barbarino | A45D 40/02 |
| 12,496,204 | B2 * | 12/2025 | Barbarino | A45D 34/04 |
| 12,538,993 | B1 * | 2/2026 | Prickett | A47G 21/10 |
| 2006/0285911 | A1 | 12/2006 | Demellier | |
| 2010/0228362 | A1 * | 9/2010 | Pathak | A47G 21/02 623/65 |
| 2013/0297022 | A1 * | 11/2013 | Pathak | A61B 5/1101 623/14.13 |
| 2014/0052275 | A1 * | 2/2014 | Pathak | A61F 4/00 623/65 |
| 2015/0300394 | A1 * | 10/2015 | Pathak | H01H 36/0013 403/328 |
| 2015/0323856 | A1 | 11/2015 | Nordhaug | |
| 2016/0242679 | A1 * | 8/2016 | Pathak | A61B 5/1101 |
| 2016/0381271 | A1 | 12/2016 | Cheng et al. | |
| 2017/0055885 | A1 * | 3/2017 | Shoeb | A61B 5/7264 |
| 2017/0100272 | A1 * | 4/2017 | Pathak | B25J 11/0045 |
| 2017/0157774 | A1 * | 6/2017 | Pathak | B25J 1/04 |
| 2017/0348127 | A1 * | 12/2017 | Pathak | A61B 5/4836 |
| 2018/0014958 | A1 * | 1/2018 | Pathak | A61B 5/1101 |
| 2018/0058536 | A1 * | 3/2018 | Pathak | A61B 5/4836 |
| 2018/0064597 | A1 * | 3/2018 | Pathak | A61B 5/1101 |
| 2018/0311062 | A1 * | 11/2018 | Pathak | G06F 3/017 |
| 2018/0344497 | A1 * | 12/2018 | Pathak | A61B 5/6825 |
| 2019/0000251 | A1 * | 1/2019 | Pathak | A47G 21/08 |
| 2019/0151129 | A1 * | 5/2019 | Pathak | A47G 21/02 |
| 2019/0365551 | A1 * | 12/2019 | Pathak | G06F 3/017 |
| 2020/0015610 | A1 * | 1/2020 | Pathak | A61B 5/6887 |
| 2020/0085168 | A1 * | 3/2020 | Pang | A61H 1/0285 |
| 2020/0146922 | A1 * | 5/2020 | Pathak | A61B 5/1101 |
| 2021/0298982 | A1 * | 9/2021 | Pathak | G05B 15/02 |
| 2022/0095775 | A1 * | 3/2022 | Lee | A46B 13/02 |
| 2024/0215702 | A1 * | 7/2024 | Barbarino | B05B 12/122 |
| 2024/0215703 | A1 * | 7/2024 | Barbarino | A45F 5/1566 |
| 2024/0215704 | A1 * | 7/2024 | Barbarino | A45D 40/02 |
| 2024/0215705 | A1 * | 7/2024 | Barbarino | A45D 40/00 |
| 2024/0216159 | A1 * | 7/2024 | Barbarino | A45D 34/04 |
| 2024/0218963 | A1 * | 7/2024 | Barbarino | F16M 11/18 |
| 2024/0219933 | A1 * | 7/2024 | Barbarino | A45D 34/04 |
| 2025/0040683 | A1 * | 2/2025 | Barbarino | A45D 40/00 |
| 2025/0040686 | A1 * | 2/2025 | Barbarino | G01P 13/00 |
| 2025/0040687 | A1 * | 2/2025 | Barbarino | A45D 34/00 |
| 2025/0040832 | A1 * | 2/2025 | Barbarino | A45D 34/04 |
| 2025/0044318 | A1 * | 2/2025 | Barbarino | G01P 13/00 |
| 2025/0044319 | A1 * | 2/2025 | Barbarino | G01P 13/00 |
| 2025/0221512 | A1 * | 7/2025 | Yoon | B25G 3/36 |
| 2026/0060461 | A1 * | 3/2026 | Wollenberger | A47G 21/04 |

OTHER PUBLICATIONS

International Search Report and Written Opinion issued Oct. 21, 2024, in International PCT Application No. PCT/US2024/040355.

* cited by examiner

COSMETIC SECUREMENT DEVICE FOR STABILIZATION OF COSMETIC APPLICATOR CONFIGURED FOR USERS WITH LIMITED MOBILITY

FIELD

The present disclosure describes a system and features related to a device for modifying, mitigating, altering, reducing, compensation for, or the like, the movement of a cosmetic applicator caused by unintentional movements, tremors, limited mobility, or the like of a user.

BACKGROUND

Unintentional movements of the human body, or human tremors, can occur in individuals suffering from motion disorders or even healthy individuals. Due to these unintentional movements, a person may have difficulty in performing a task that requires care and precision, such as applying a cosmetic composition to a part of the body, such as the face, hands, or feet.

Therefore, there is a need for a solution that allows application of a cosmetic composition that is compatible with the diverse and disposable nature of cosmetic applicators.

SUMMARY

In one embodiment, the present disclosure is directed to a cosmetic securement device for stabilization of a cosmetic applicator, comprising: a motion stabilizer handle; an internal sleeve configured to be removably inserted into the motion stabilizer handle; and an adapter coupled to a first end of the cosmetic securement device, wherein the internal sleeve includes at least one positioning joint at a first end of the internal sleeve, the first end of the internal sleeve aligning with a first end of the motion stabilizer handle when the internal sleeve is inserted into the motion stabilizer handle, wherein the motion stabilizer handle includes at least one releasable locking mechanism configured to secure the internal sleeve inside the motion stabilizer handle, and wherein the adapter is configured to hold a plurality of different types of cosmetic applicators.

In one embodiment, the present disclosure is directed to the cosmetic securement device, wherein the at least one releasable locking mechanism includes a snap-fit joint formed by the internal sleeve and the motion stabilizer handle.

In one embodiment, the present disclosure is directed to the cosmetic securement device, wherein the motion stabilizer handle includes a button and wherein depressing the button releases the internal sleeve from the at least one releasable locking mechanism.

In one embodiment, the present disclosure is directed to the cosmetic securement device, wherein the button is provided at a second end of the motion stabilizer handle.

In one embodiment, the present disclosure is directed to the cosmetic securement device, wherein the at least one positioning joint includes a flexible metal wire core.

In one embodiment, the present disclosure is directed to the cosmetic securement device, wherein the at least one positioning joint includes at least one ball joint.

In one embodiment, the present disclosure is directed to the cosmetic securement device, wherein the adapter is coupled to the at least one positioning joint when the internal sleeve is inserted into the motion stabilizer handle.

In one embodiment, the present disclosure is directed to a cosmetic securement device, comprising a motion stabilizer handle; an internal sleeve configured to be removably inserted into the motion stabilizer handle; and an adapter coupled to a first end of the cosmetic securement device, wherein the internal sleeve includes at least one positioning joint at a first end of the internal sleeve, the first end of the internal sleeve aligning with a first end of the motion stabilizer handle when the internal sleeve is inserted into the motion stabilizer handle, wherein the internal sleeve includes at least one sensor configured to detect movement caused by a user, wherein the motion stabilizer handle includes at least one releasable locking mechanism configured to secure the internal sleeve inside the motion stabilizer handle, and wherein the adapter is configured to hold a plurality of different types of cosmetic applicators.

In one embodiment, the present disclosure is directed to the cosmetic securement device, wherein the at least one sensor includes an inertial sensor and a distributed motion sensor.

In one embodiment, the present disclosure is directed to the cosmetic securement device, wherein the movement data includes an orientation and an acceleration of the motion stabilizer handle.

In one embodiment, the present disclosure is directed to the cosmetic securement device, wherein the at least one releasable locking mechanism includes a snap-fit joint formed by the internal sleeve and the motion stabilizer handle.

In one embodiment, the present disclosure is directed to the cosmetic securement device, wherein the motion stabilizer handle includes a button and wherein depressing the button releases the internal sleeve from the at least one releasable locking mechanism.

In one embodiment, the present disclosure is directed to the cosmetic securement device, wherein the at least one positioning joint includes a flexible wire core.

In one embodiment, the present disclosure is directed to the cosmetic securement device, wherein the adapter is coupled to the at least one positioning joint when the internal sleeve is inserted into the motion stabilizer handle.

In one embodiment, the present disclosure is directed to a cosmetic securement device for stabilization of a cosmetic applicator, comprising a motion stabilizer handle; an internal sleeve configured to be removably inserted into the motion stabilizer handle; and an adapter coupled to a first end of the cosmetic securement device, wherein the internal sleeve includes at least one sensor configured to detect movement caused by a user, circuitry configured to determine a compensation movement to offset the detected movement, and at least one motion generation device embedded in a first end of the internal sleeve configured to control a motion of the adapter according to the determined compensation movement, wherein the first end of the internal sleeve aligns with a first end of the motion stabilizer handle when the internal sleeve is inserted into the motion stabilizer handle, wherein the motion stabilizer handle includes at least one releasable locking mechanism configured to secure the internal sleeve inside the motion stabilizer handle, and wherein the adapter is configured to hold a plurality of different types of cosmetic applicators.

In one embodiment, the present disclosure is directed to the cosmetic securement device, wherein the at least one sensor includes an inertial sensor and a distributed motion sensor.

In one embodiment, the present disclosure is directed to the cosmetic securement device, wherein the at least one releasable locking mechanism includes a snap-fit joint formed by the internal sleeve and the motion stabilizer handle.

In one embodiment, the present disclosure is directed to the cosmetic securement device, wherein the motion stabilizer handle includes a button and wherein depressing the button releases the internal sleeve from the at least one releasable locking mechanism.

In one embodiment, the present disclosure is directed to the cosmetic securement device, wherein the button is provided at a second end of the motion stabilizer handle.

In one embodiment, the present disclosure is directed to the cosmetic securement device, wherein the adapter is coupled to the motion generation device when the internal sleeve is inserted into the motion stabilizer handle.

BRIEF DESCRIPTION OF THE DRAWINGS

A more complete appreciation of the embodiments and many of the attendant advantages thereof will be readily obtained as the same becomes better understood by reference to the following detailed description when considered in connection with the accompanying drawings, wherein.

DETAILED DESCRIPTION

The present disclosure describes a cosmetic applicator system that minimizes, modifies, mitigates, alters, reduces, compensates for, or the like unintentional movements by stabilizing, orienting, operating, controlling, etc. an applicator for a user and is also designed to be flexible to accommodate different types of commercially available cosmetic applications. The present disclosure further describes a system and features to enhance the functionality of such a cosmetic applicator system.

The basic features and operation of a motion stabilizing device for a cosmetic applicator is described in U.S. Pat. No. 11,458,062, which is incorporated herein by reference.

Figure 1:
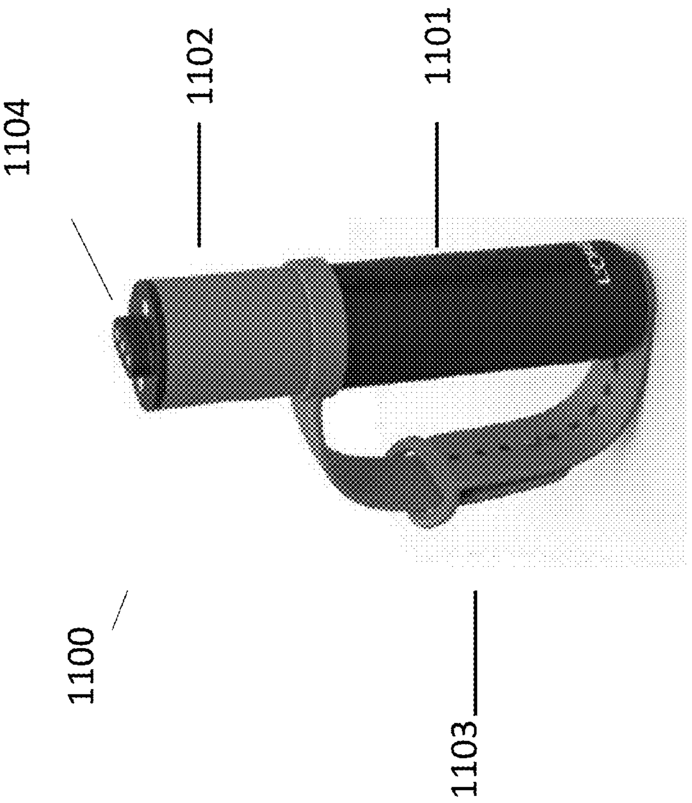
FIG. 1 shows a conventional motion stabilizing device.

FIG. 1 shows a conventional motion stabilizing device 1100, which serves as a base unit for receiving a cosmetic applicator according to an embodiment. The device 1100 includes a handle portion 1101, a receiver portion 1102 and a strap 1103. The receiver portion 1102 includes an interface 1104, shown as a male connector that couples with a cosmetic applicator, which will be discussed in detail below. The receiver portion could be utilized for communication between the base unit and the applicator. The connection to an adaptor and/or an applicator could be accomplished with a mechanical coupling, such as screw-in or snap-fit, or it could be accomplished with magnets.

Figure 2:
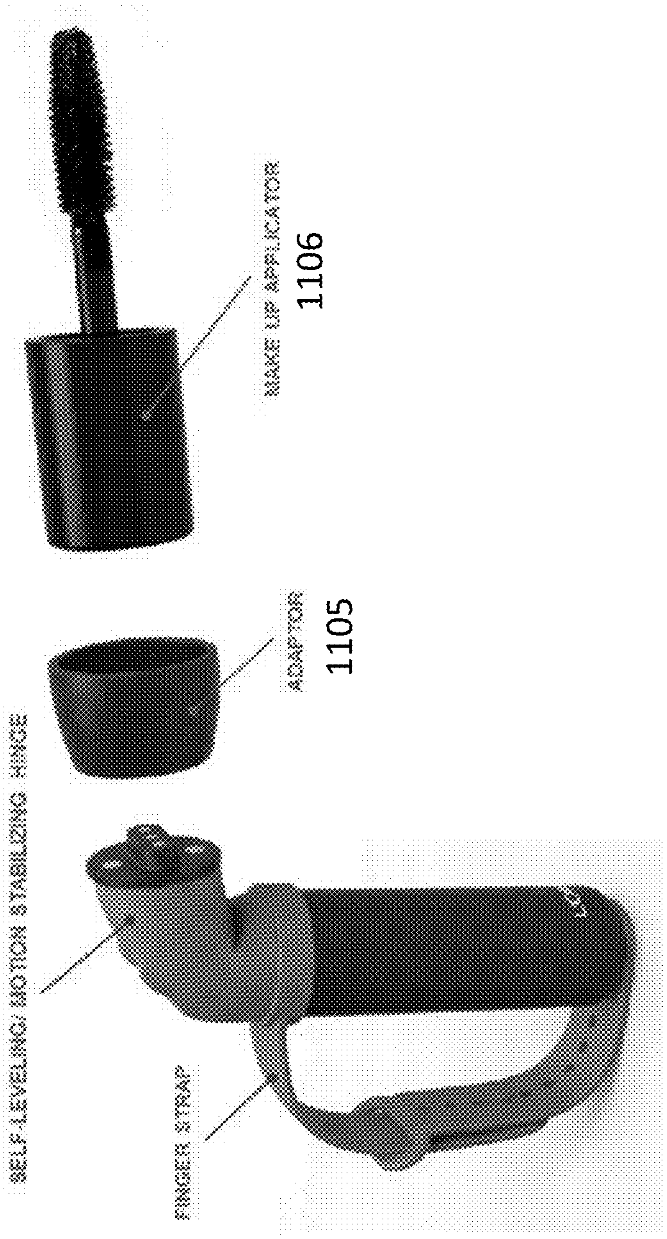
FIG. 2 shows how the conventional motion stabilizing device couples with an adaptor and a make-up applicator.

FIG. 2 shows how the device 1100 couples with an adaptor 1105 and a make-up applicator 1106. It can be seen that the adaptor fits over the exposed end of the receiver portion 1102. The adaptor includes electrical mating connectors (a female connector—not shown) in a recessed portion to make contact with the electric interface of the receiver portion 1101.

As shown in FIG. 2, the receiver portion 1102 is configured to contort, articulate, reposition, etc., between an upright posture (as shown in FIG. 1) and an angled posture (as shown in FIG. 2). This is accomplished with a hinge mechanism contained inside the receiver portion 1102. FIG. 2 shows that the hinge mechanism is a self-leveling/motion stabilizing hinge.

Figure 3A:
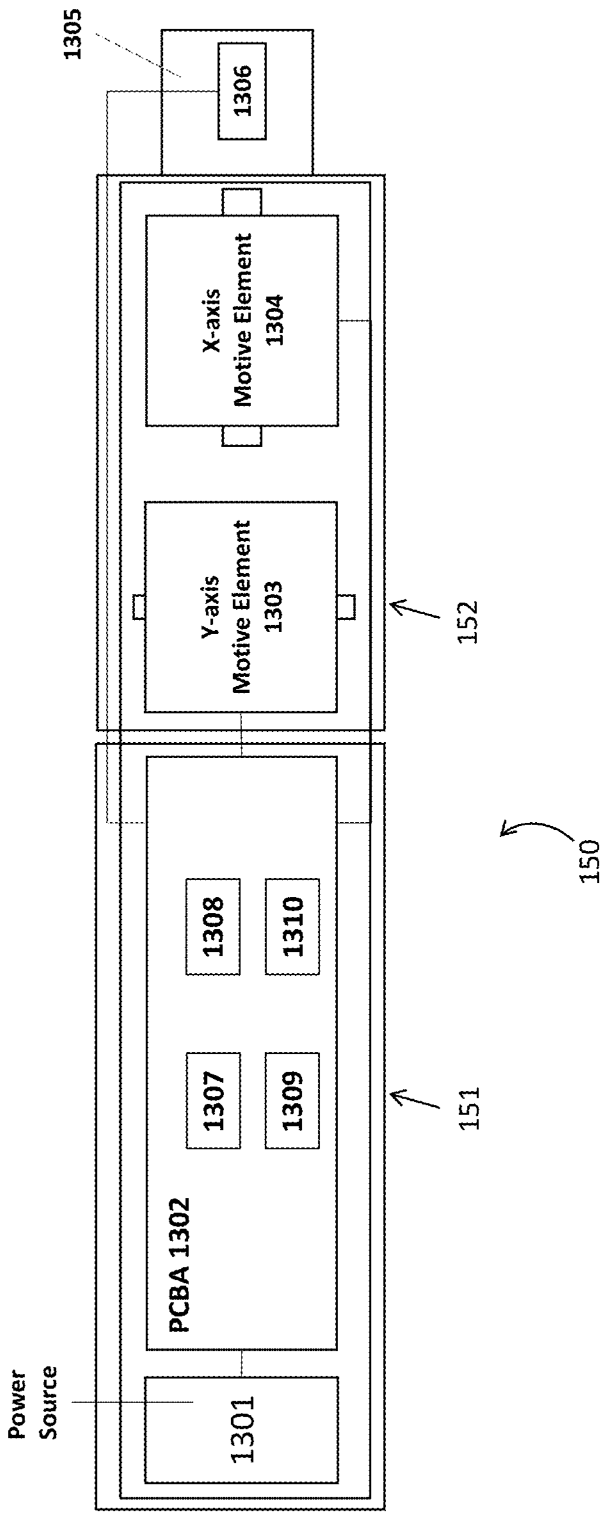
FIG. 3A shows a diagram of the internal components of a motion stabilizing device according to one embodiment.

FIG. 3A shows a diagram of the internal components of device 1100 according to one embodiment. In the handle portion, the device includes a power source 1301, which may be a battery or the like. The device includes a printed circuit board assembly (PCBA) 1302, which may include positional sensor circuitry 1307, reader circuitry 1308, control circuitry 1309, and communication interface 1310, as understood in the art.

For instance, as the sensor circuitry 1307, the PCBA may include at least one inertial sensor and at least one distributed motion sensor to detect unintentional muscle movements and measure signals related to these unintentional muscle movements that are created when a user adversely affects motion of the applicator. These sensors also detect the motion of the stabilized output relative to device. The control circuitry sends voltage commands in response to the signals to the motion generating elements (described below) to cancel the user's tremors or unintentional muscle movements. This cancellation maintains and stabilizes a position of the applicator, keeping it stable.

One of ordinary skill in the art readily recognizes that a system and method in accordance with the present invention may utilize various implementations of the control circuitry and the sensor circuitry and that would be within the spirit and scope of the present invention. In one embodiment, the control circuitry 1309 comprises an electrical system capable of producing an electrical response from sensor inputs such as a programmable microcontroller or a field-programmable gate array (FPGA). In one embodiment, the control circuitry comprises an 8-bit ATMEGA8A programmable microcontroller manufactured by Atmel due to its overall low-cost, low-power consumption and ability to be utilized in high-volume applications.

In one embodiment, the at least one inertial sensor in the sensor circuitry is a sensor including but not limited to an accelerometer, gyroscope, or combination of the two. In one embodiment, the at least one distributed motion sensor in the sensor circuitry is a contactless position sensor including but not limited to a hall-effect magnetic sensor.

The system created by the combination of the sensor circuitry, the control circuitry, and the motion generating elements may be a closed-loop control system that senses motion and acceleration at various points in the system and feeds detailed information into a control algorithm that moves the motion-generating elements appropriately to cancel the net effect of a user's unintentional muscle movements and thus stabilize the position of the applicator. The operation and details of the elements of the control system and control algorithm are understood in the art, as described in U.S. PG Publication 2014/0052275A1, incorporated herein by reference.

The communication interface 1310 may include a network controller such as BCM43342 Wi-Fi, Frequency Modulation, and Bluetooth combo chip from Broadcom, for interfacing with a network.

In the receiver portion of the device, there may be two motive elements to allow 3-dimensional movement of the receiver as anti-shaking movement. The two motive elements include a y-axis motive element 1303 and an x-axis motive element 1304, each being connected to and controlled by the PCBA 1302. Each of the motive elements may be servo motors as understood in the art. The device further includes end effector coupling 1305, which is configured to couple with the adaptor 1105. The end effector coupling 1305 may include a radiofrequency identification (RFID) reader 1306, configured to read an RFID tag, which may be included with the applicator, as will be discussed below.

Figure 3B:
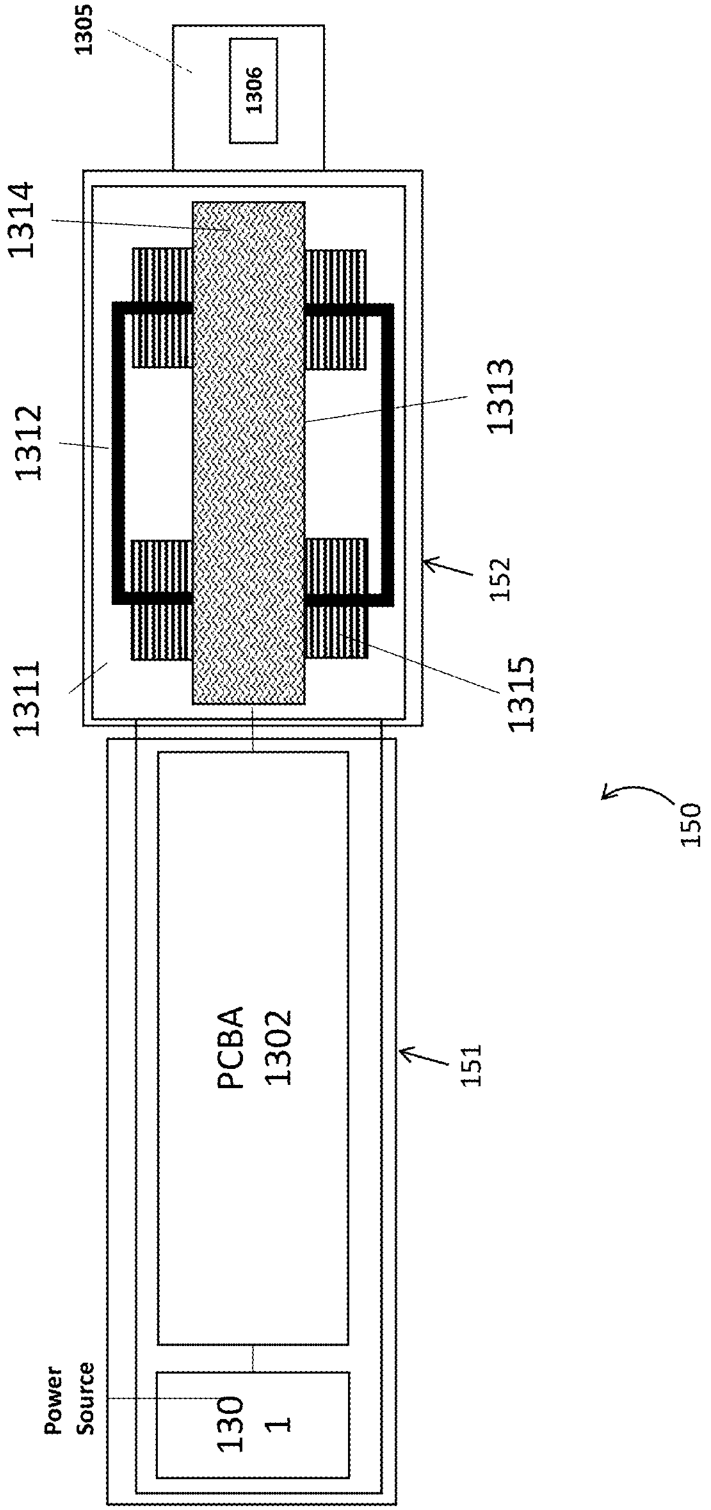
FIG. 3B shows a diagram of an alternative embodiment of the motion stabilizing device in which a receiver portion includes an electromagnetic positioner.

FIG. 3B shows a diagram of an alternative embodiment of the device 1100 in which the receiver portion includes an electromagnetic positioner 1311 instead of the motive elements shown in FIG. 3A. The electromagnetic positioner 1311 may include U-shaped magnetic cores 1312 arrayed around a non-magnetic tube 1313, which is filled with a magnetic fluid 1314. Each of the magnetic cores has arm portions that are surrounded by windings 1315. The magnetic cores may be controlled by the control circuitry in the PCBA 1302 to act as a controllable active magnetic field-generating structure which is used to generate a variable magnetic field that acts upon the magnetic fluid, causing it to be displaced, thereby enabling the armature to be moved to a desired coordinate position and/or orientation. The details of implementing the electromagnetic positioner 1311 may be found in U.S. Pat. No. 6,553,161, which is incorporated herein by reference.

The below embodiments provide a modular motion stabilizing device wherein the internal motion stabilization components can be easily removed from the handle (e.g., swapped out) in order to provide a more positive and adaptive user experience and reduce the time needed to set up the system for use.

In one embodiment, the present disclosure is directed towards a cosmetic securement device for stabilization of a cosmetic applicator. The cosmetic applicator can be used for a variety of cosmetics and cosmetic applications, including, but not limited to, mascara, eyeliner, eyebrow products, lip products (lipstick, lip gloss, lip liner, etc.), skin products, and/or hair products. In one embodiment, the cosmetic securement device can include an adapter coupled to a motion stabilizer device, wherein the adapter can hold a cosmetic product. The motion stabilizer device can be, for example, a handle that can counteract unintentional motions such as tremors or spasms. These motions can interfere with the application of cosmetics and can also make it difficult to generally interact with cosmetic products or tools. For example, many cosmetic products require a twisting motion or force to be applied to open or extrude the product. It can be difficult for users to achieve the range of motion or the precision necessary to apply these forces to the cosmetic. In one embodiment, the cosmetic applicator can hold a cosmetic and can enable the proper force to be applied to the cosmetic to open, close, mix, stir, blend, extrude, or achieve other similar functions necessary for application.

In one embodiment, the present disclosure is directed towards a cosmetic securement device including a motion stabilizer handle wherein components of the motion stabilizer handle can be modified for users with varying needs. In some cases, users may not need the full functionality of the motion stabilizer handle as described with reference to FIG. 3A and FIG. 3B. For instance, users may prefer full or partial control over the movement of the cosmetic applicator rather than automatic motion stabilization. The automatic motion stabilization provided by a motion stabilizer device may be counteractive to a desired usage of the cosmetic applicator. In addition, a user with a different range of motion may need a different level or type of motion stabilization. For example, a user with reduced grip strength may need a cosmetic securement device to hold a cosmetic tool in a fixed position but may not need motion stabilization once the cosmetic tool is placed in an adapter. Therefore, it can be advantageous to provide a cosmetic securement device wherein motion stabilization components can be removed or exchanged from the motion stabilizer handle for varying functionality.

The motion stabilization components of the cosmetic securement device can include the components shown in the motion stabilizer in FIG. 3A and FIG. 3B. For example, the motion stabilization components can include the power source 1301, the printed circuit board assembly (PCBA) 1302, which may include positional sensor circuitry 1307, reader circuitry 1308, control circuitry 1309, and communication interface 1310, motive elements 1303, 1304, end effector coupling 1305 and RFID reader 1306, electromagnetic positioner 1311 including U-shaped magnetic cores 1312 arrayed around non-magnetic tube 1313, which is filled with a magnetic fluid 1314, and windings 1315 surrounding the magnetic cores. In an embodiment, one or more of the motion stabilization components are removably coupled to the interior of the cosmetic securement device.

Figure 4:
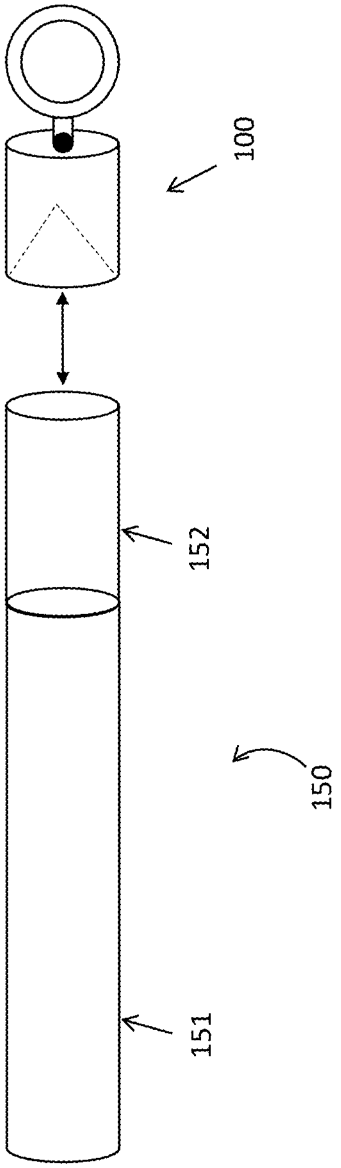
FIG. 4 shows an overview of a cosmetic securement device with a universal adapter handle connection system.

FIG. 4 shows an overview of a cosmetic securement device including a motion stabilizer device 150 and a cosmetic adapter 100, according to one embodiment of the present disclosure. The motion stabilizer device 150 can include at least one of a handle portion 151 and a hinge portion 152 (receiver portion). The handle portion 151 can be functionally similar to the handle portion 1101 shown in FIG. 1. The receiver portion 152 can be functionally similar to the receiver portion 1102 shown in FIG. 1. In an embodiment, the motion stabilizer device 150 as a whole is referred to herein as a motion stabilizer handle. In an embodiment, the cosmetic securement device includes a cosmetic adapter 100, wherein the adapter 100 can be coupled to the receiver portion 152 of the motion stabilizer device 150. In an embodiment, the cosmetic adapter 100 holds a cosmetic tool or product. In one embodiment, the cosmetic adapter 100 can be a universal adapter configured to hold different types of cosmetic products. For example, the adapter 100 can include a ring-shaped holder. Various configurations of the adapter 100 can be used for different cosmetics and tools. For example, the shape and dimensions of the cosmetic holder can be configured for different cosmetic products. The adapter 100 can be easily attached to and removed from the motion stabilizer device. The basic features and operation of the cosmetic securement device of FIG. 4 are described in co-pending U.S. patent application Ser. Nos. 18/091,882; 18/091,920; 18/091,843; 18/091,925; 18/148,957; and Ser. No. 18/148,880; and Ser. No. 18/148,930, which are incorporated herein by reference.

In one embodiment, the adapter 100 is coupled to the receiver portion 152 of the motion stabilizer device 150 via a magnetic attachment. The base or bottom end of the adapter 100 can form a chamber that can fit over a projection at the tip of the receiver portion 152. The base of the adapter can include at least one magnet, wherein the at least one magnet can be attracted to and attach to a magnet in the receiver portion 152. In one embodiment, the chamber formed at the base of the adapter 100 can fit over the receiver portion 152 in more than one orientation. The chamber can be a hollow area within the body of the adapter that is fully contained by the walls of the adapter 110. The chamber can be approximately conical in shape. In one embodiment, the chamber can be cylindrical. The chamber can be configured to fit over a projection on one end of the motion stabilizer. The chamber can be used to align and guide the attachment of the cosmetic applicator to the motion stabilizer. The fit of the chamber over and around the projection on the end of the motion stabilizer limits lateral motion that would misalign the cosmetic applicator and the motion stabilizer. It can be easier for a user to align the chamber over the end of the motion stabilizer than it would be for the user to align the edges of a circular face of the adapter with the edges of a circular face of the motion stabilizer. The chamber can have rotational symmetry such that the cutout can be placed over the end of the motion stabilizer in any orientation or at any degree of rotation around the axis of the chamber. In one embodiment, the bottom end of the adapter body can include additional physical structures that can align, guide, and fix the adapter to the motion stabilizer.

Figure 5B:
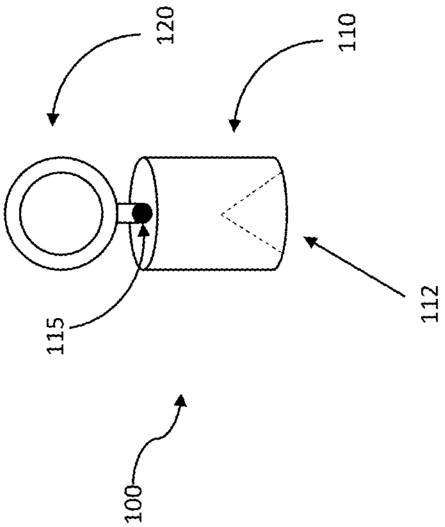
FIG. 5B is a transparent side view of the adapter, according to one embodiment.
Figure 5A:
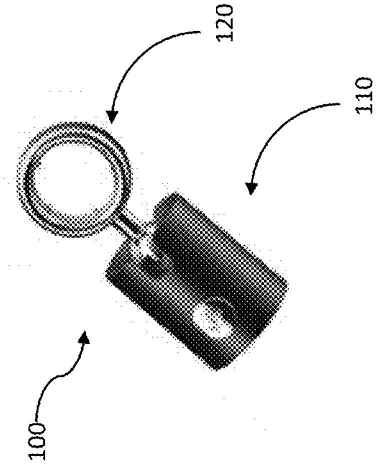
FIG. 5A shows an illustration of an adapter, according to one embodiment.

FIG. 5A shows an illustration of adapter 100, according to one embodiment of the present disclosure. The adapter 100 can include an adapter body 110, wherein the adapter body 110 can be connected to the motion stabilizer 150. The adapter body 110 can be connected to or can form the base or body of a cosmetic holder 120. Each of these components will be discussed in further detail herein. Various configurations of the adapter 100 can be used for different cosmetics and tools. For example, the shape and dimensions of the cosmetic holder 120 can be configured for different cosmetic products. The adapter 100 can be easily attached to and removed from the motion stabilizer, as will be discussed herein. In one embodiment, the adapter 100 can broaden the range of motion of a cosmetic applicator to enable movements that are necessary for cosmetic application. In some embodiments, the adapter 100 can be attached to a stand or carriage for further actions to be performed with a cosmetic held by the cosmetic applicator.

FIG. 5B is a transparent side view of the adapter 100, according to one embodiment of the present disclosure. The adapter body 110 can be shaped approximately as a right cylinder. A first end of the adapter can be attached to one end of a motion stabilizer. The motion stabilizer can be a cylindrical rod forming a handle for a user to grasp. The first end can also be referred to hereinafter as a bottom end or a base of the adapter. The bottom end of the adapter body 110 can include at least one magnet, wherein the at least one magnet can be attracted to and attach to a magnet in the motion stabilizer. The bottom end of the adapter body 110 can include additional physical structures that can align, guide, and fix the adapter to the motion stabilizer. In one embodiment, the bottom end of the adapter body 110 can form a chamber 112, as illustrated in the transparent view of FIG. 5B. The chamber can be a hollow area within the body of the adapter 110 that is fully contained by the walls of the adapter 110. The chamber 112 can be approximately conical in shape. In one embodiment, the cutout can be cylindrical. The chamber 112 can be configured to fit over a projection on one end of the motion stabilizer. The chamber 112 can be used to align and guide the attachment of the cosmetic applicator to the motion stabilizer. The fit of the chamber 112 over and around the projection on the end of the motion stabilizer limits lateral motion that would misalign the cosmetic applicator and the motion stabilizer. It can be easier for a user to align the chamber 112 over the end of the motion stabilizer than it would be for the user to align the edges of the circular face of the adapter with the edges of the circular face of the motion stabilizer. The chamber 112 can have rotational symmetry such that the cutout can be placed over the end of the motion stabilizer in any orientation or at any degree of rotation around the axis of the chamber 112. In one end, a magnet can be fixed at the tip of the chamber, inside the body of the adapter. The magnet at the tip of the cutout can be attached to a magnet at the tip of the projection on the end of the motion stabilizer.

The cosmetic holder 120 can be located at a second end of the cosmetic applicator. In one embodiment, the cosmetic holder 120 can be a ring, wherein a cosmetic tool or product can be inserted into the ring. Many cosmetic tools, such as mascara wands, lipstick applicators, concealer applicators, and cosmetic pencils, are approximately cylindrical. In one embodiment, the ring can secure the cosmetic tools at the widest part of the tool. A ring-shaped holder can also hold cosmetic tools of varying shapes, such as cuboids. In one embodiment, the cosmetic holder 120 can include one or more projections along the inner wall of the holder and extending outward into the center of the holder. Contact and friction between the one or more projections and an inserted cosmetic tool can result in a more secure grip or hold of the cosmetic holder around the inserted cosmetic tool. In some embodiments, the inner wall of the cosmetic holder 120 can be lined with a material that can improve the grip or hold of the cosmetic holder around the inserted cosmetic tool. The improved grip can be a result of a material property, such as a coefficient of friction or a material deformation. For example, the inner wall can be lined with rubber or silicon. In one embodiment, the lining material can be a textured material with grooves, ridges, bumps, or similar features that prevent movement or slippage of the cosmetic tool once it is inserted into the cosmetic holder 120.

Various cosmetic holder configurations are compatible with the cosmetic applicator 100. In one implementation, the holder can be an open ring or a C-shaped holder. In one embodiment, the holder can be a loop, wherein the ends of the loop can overlap. In one embodiment, the holder can be one or more coiled loops. In one embodiment, the cosmetic holder 120 can be a tube or sheath forming a chamber inside the tube, wherein a cosmetic tool or product can be inserted into the chamber. In one embodiment, the tube can be closed on one end to contain a cosmetic tool or product in the chamber. In one example, the tube can be approximately cylindrical. In one example, the sheath can be a partial cylinder, such as a half-cylinder that does not wrap fully around the inserted cosmetic. In one embodiment, the size of the cosmetic holder 120 can be modified. For example, the cosmetic holder 120 can be a round holder, wherein the diameter of the holder can be modified to accommodate different cosmetic tools. A pushing force on a point along the outside of the holder can compress the holder to that of a smaller diameter. A pulling force on a point along the inside of the holder can expand the holder to that of a larger diameter. In one embodiment, the force can be applied at a single point along the holder to enable one-handed modification of the holder diameter. In one implementation, a user can be provided with a number of cosmetic holders, wherein each cosmetic holder has different dimensions or shapes for different cosmetic tools or products. A cosmetic holder 120 can be removed from the adapter body 110 and replaced with another of suitable configuration.

In one embodiment, the cosmetic holder 120 can be attached to the adapter body 110 with a joint 115, such as a ball joint. The ball joint can enable movement of the cosmetic holder 120 relative to the adapter body 110. For example, the cosmetic holder 120 can be rotated in place or can pivot to form an angle with the adapter body 110. The joint can be configured for continuous motion of the cosmetic holder 120 or for discrete steps of movement. According to some embodiments, the motion of the cosmetic holder 120 can be constrained. For example, the adapter 110 can form a walled channel, wherein the joint is disposed inside the walled channel. The walls of the channel can constrain movements of the joint and/or the cosmetic holder 120. In one embodiment, the joint 115 can be a motorized component. The cosmetic holder 120 can move as a result of the motorized component without requiring external force from a user.

Figure 5D:
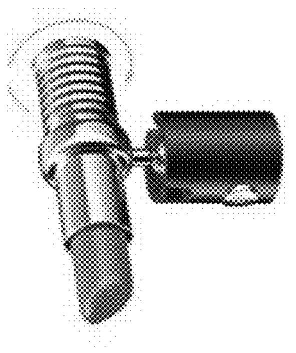
FIG. 5D shows how the adaptor holds a specific cosmetic applicator, according to an embodiment.
Figure 5C:
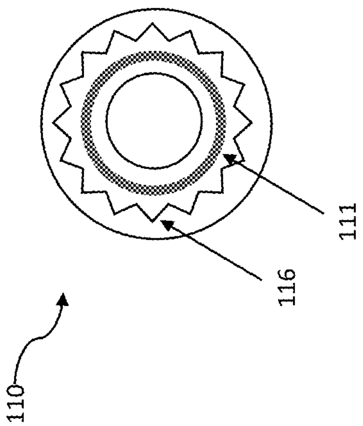
FIG. 5C is a view of the bottom face of the adapter body, according to one embodiment.

FIG. 5C is a view of the bottom face of the adapter body 110, according to one embodiment of the present disclosure. The bottom face of the adapter body 110 can be approximately a circle given that the adapter is a right cylinder. A magnet 111 can be disposed on the bottom face of the adapter. In one embodiment, the magnet 111 can be a uniformly ring-shaped magnet, as illustrated in FIG. 5C. For example, the magnet 111 can have the shape of a washer. The ring-shaped magnet 111 can be attracted to and attach to a magnet disposed along the circumference of one end of the motion stabilizer. In some embodiments, the adapter body 110 can be attached to the motion stabilizer in any orientation because of the ring-shaped magnet 111. The adapter body 110 can be attached to the motion stabilizer with any rotation of the adapter 100 around the central axis of the adapter. In one embodiment, the adapter 100 can be a universal adapter and can attach a magnetic end of the motion stabilizer in any orientation regardless of the positioning and/or polarity of magnets at the end of the motion stabilizer. Any portion of the ring-shaped magnet 111 at the base of the adapter can contact the magnets on the motion stabilizer to attach the adapter to the motion stabilizer.

The ring-shaped magnet 111 of the present disclosure presents an advantage over traditional adapters for motion stabilizer. For example, certain motion stabilizers can include two magnets located diametrically opposite to each other on a circular face of the motion stabilizer. Most traditional adapters include two magnets at the base for attachment to a motion stabilizer. The adapter can only be attached to the motion stabilizer if the two magnets on the motion stabilizer align with the two magnets in the same position on the adapter. In some implementations, the polarity of the magnets on the motion stabilizer can also differ such that each magnet on the motion stabilizer will only be attracted to one of the two magnets on the adapter. The limitations on the orientation of the traditional adapter can pose issues for users attempting to attach the adapter to the motion stabilizer. For example, users may lack the precision of movement needed to align the magnets as needed for attachment. In addition, the limitations on the orientation of the traditional adapter means that the orientation of the tool or instrument that is held by the applicator is also limited. When applying cosmetic products to or near the face, it can be desired that the applicator can be fixed at various angles and orientations or that the orientation of the applicator can be adjusted. For example, certain mascara wands are curved. The mascara wand should contact the eyelashes such that the curvature of the wand conforms to the curvature of the eye. It can be very difficult to achieve this position if the adapter holding the mascara wand can only be attached to the motion stabilizer in one orientation, as with traditional adapters with a limited number of magnets in set positions. In contrast, an adapter with a ring-shaped magnet, as in FIG. 5C, can be attached to the motion stabilizer in any orientation. The adapter can be rotated until the mascara wand, or any other cosmetic tool, is in a desired orientation for application and then attached to the motion stabilizer with contact between the ring-shaped magnet and any magnets disposed on the face of the motion stabilizer. The motion stabilizer can be maneuvered in various positions while the attached applicator and cosmetic also move. For example, the orientation of the attached applicator and the cosmetic can change as the user applies the cosmetic. The attachment of the applicator to the motion stabilizer without orientation expands the range of movement of the attached cosmetic.

In one embodiment, the adapter body 110 can include a ring of gears, teeth, or similar alignment structures 116. The alignment structures 116 can be located at the base of the adapter and can be concentric with the ring-shaped magnet 111. In one embodiment, the alignment structures can be located along the inner wall of the cutout at the bottom end of the adapter. In some embodiments, the alignment structures 116 can fit into or interlock with corresponding alignment structures on the motion stabilizer when the adapter is attached to the motion stabilizer. The alignment structures 116 can limit the rotation of the cosmetic applicator once the adapter has been attached to the motion stabilizer. Certain motion stabilizers can rotate in order to counteract any rotational force applied to the motion stabilizer so that an attachment to the motion stabilizer (such as the cosmetic applicator) remains steady. The "anti-rotation" mechanism can be useful for users who experience sudden, involuntary movements while holding the motion stabilizer. In one embodiment, the alignment structures 116 can be a ring of raised nubs or teeth-like structures that can fit into corresponding grooves or receptacles at the end of the motion stabilizer that is attached to the base of the adapter. In one embodiment, the alignment structures 116 can be a ring of recessed structures or a combination of raised and recessed structures that can fit into corresponding raised and/or recessed structures at the end of the motion stabilizer. The fitting of the alignment structures 116 into complementary structures at the end of the motion stabilizer can fix the cosmetic applicator in place when the adapter has been attached to the motion stabilizer. Any rotation of the motion stabilizer in order to counteract involuntary user movement will thus be carried through to the cosmetic applicator to maintain the orientation of the cosmetic applicator once the cosmetic applicator is attached to the motion stabilizer.

The alignment structures 116 can provide a range of discrete orientations at which the adapter can be attached to the motion stabilizer. For example, the adapter can only be attached to the motion stabilizer when each of the alignment structures 116 of FIG. 5C is aligned with a corresponding recessed structure in the motion stabilizer. If the alignment structures 116 are not aligned with and sitting in the recessed structures, the adapter will not be properly attached to the motion stabilizer. However, the symmetry of the repeated alignment structures 116 can still enable the attachment of the adapter at a number of rotations (e.g., 10+ rotational options) for easy attachment.

FIG. 5D shows how the adaptor 100 holds a specific cosmetic applicator, such as a lipstick applicator within the cosmetic holder 120. While a lipstick applicator is shown, the cosmetic holder can hold numerous examples of applicators, such as mascara applicators and nail polish applicators as other examples. In contrast to the adapter 1105 of FIG. 1, it can be seen that the cosmetic holder 120 holds the applicator at perpendicular angle to the handle of the motion stabilizer 150. This provides a more relaxed and ergonomic hand position for the user when using the cosmetic applicator.

Figure 6B:
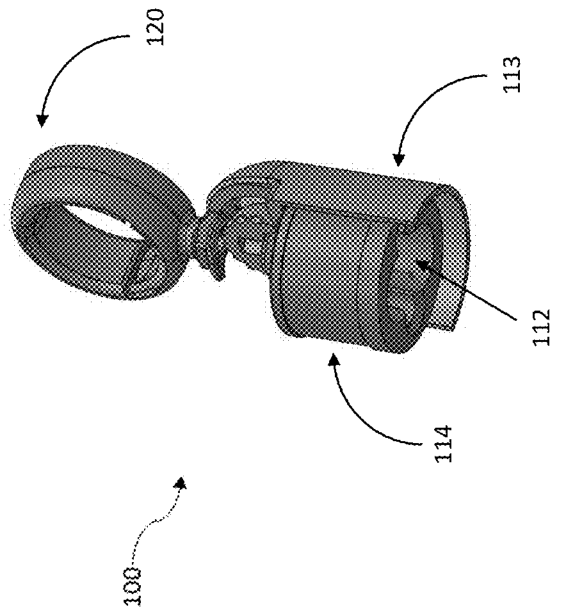
FIG. 6B is a side view of the adaptor with a cutaway view of the adaptor body, according to one embodiment.
Figure 6A:
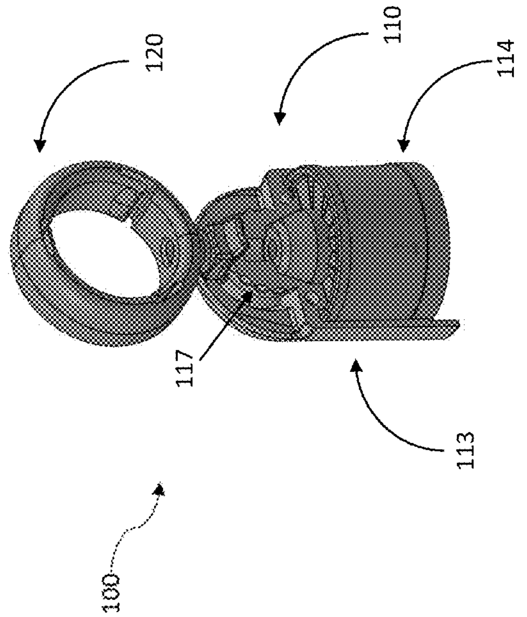
FIG. 6A is an illustration of the adaptor 100 with a cutaway view of the adaptor body 110, according to one embodiment.

FIG. 6A is an illustration of the adaptor 100 with a cutaway view of the adaptor body 110, according to one embodiment of the present disclosure. In one embodiment, the adaptor body 110 can include an outer shell 113, wherein the outer shell 113 encloses an inner body 114. The inner body 114 can be attached to a motion stabilizer via the magnetic attachment described herein with reference to FIG. 5C. In one embodiment, the cosmetic holder 120 can be attached to the outer shell 113. The attachment of the cosmetic holder 120 to the outer shell 113 can enable movement of the cosmetic holder 120 that is independent of the movement of the inner body or the motion stabilizer. The attachment of the cosmetic holder 120 to the outer shell 113 can be enclosed within the adaptor body 110. In one embodiment, the cosmetic holder 120 can be attached to the outer shell 113 along a series of detents in the outer shell. The detents can be, for example, a series of indentations, grooves, teeth, or the like, such as the indented structures 117 of FIG. 6A. The position of the cosmetic holder 120 can change by moving the cosmetic holder 120 linearly along the series of detents, such that the cosmetic holder 120 can be fixed in place at each of the detent structures 117. In one embodiment, the base of the cosmetic holder 120 can include a projection that fits into each of the detent structures 117. The projection can snap into place when positioned at or against each of the detent structures 117 to temporarily lock the cosmetic holder 120 into an angled position within a single plane. The plane of the face (opening) of the cosmetic holder 120 can stay the same while the angular position of the cosmetic holder 120 can be adjusted. A force can be applied by a user to position the cosmetic holder 120 at any of the detent structures 117. The cosmetic holder 120 can thus be angled relative to the central axis of the adaptor body 110 and the attached motion stabilizer. In one embodiment, the cosmetic holder 120 can be attached to the adaptor body 110 with a 2-axis adapter. The angle of the cosmetic holder 120 can be adjusted as described with reference to the detent structures 117. Additionally or alternatively, the plane of the opening of the cosmetic holder 120 can also be adjusted by a rotation of the cosmetic holder 120 for 2-axis movement. For example, the cosmetic holder 120 can rotate axially at or near the point of attachment to the adaptor body 110. In one embodiment, the rotation of the cosmetic holder 120 can be modulated with detents or similar structures to provide a number of fixed rotational positions of the cosmetic holder 120. For example, the cosmetic holder 120 or the adaptor body 110 can include an internal gear or ratcheting structure, wherein the cosmetic holder 120 can be rotated a number of degrees to engage the teeth of the internal gear. The cosmetic holder 120 can be temporarily locked in a rotational position when the teeth are engaged.

FIG. 6B is a side view of the adaptor 100 with a cutaway view of the adaptor body 110, according to one embodiment of the present disclosure. The inner body 114 of the adaptor body 110 can form the chamber 112, as has been described herein. Various shapes and dimensions of the chamber 112 are compatible with the present adaptor 100. In one embodiment, the outer shell 113 can extend past the end of the inner body 114. The outer shell 113 can surround the attachment point of the adaptor 100 to a motion stabilizer or other compatible structure and can prevent the adaptor 100 from being displaced from the attached structure. In some embodiments, the magnetic ring can be formed at the base of the inner body 114.

Figure 6D:
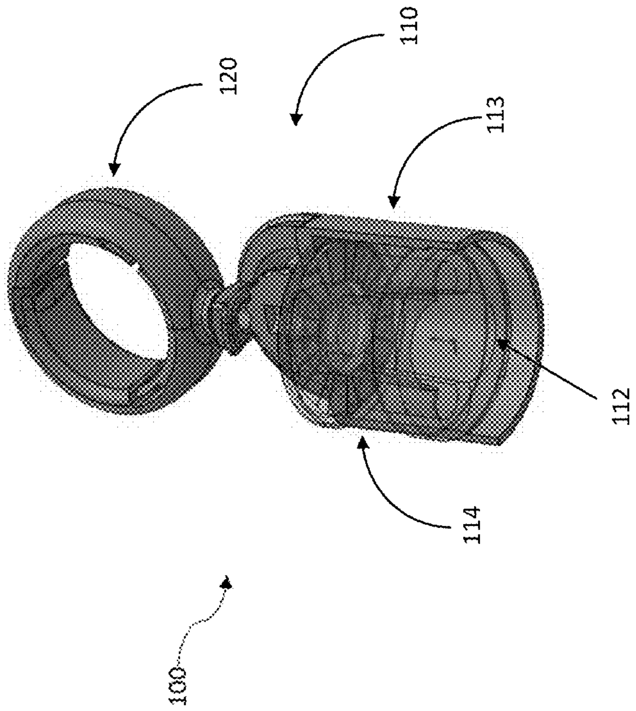
FIG. 6D is a transparent view of the inner body of the adaptor, according to one embodiment.
Figure 6C:
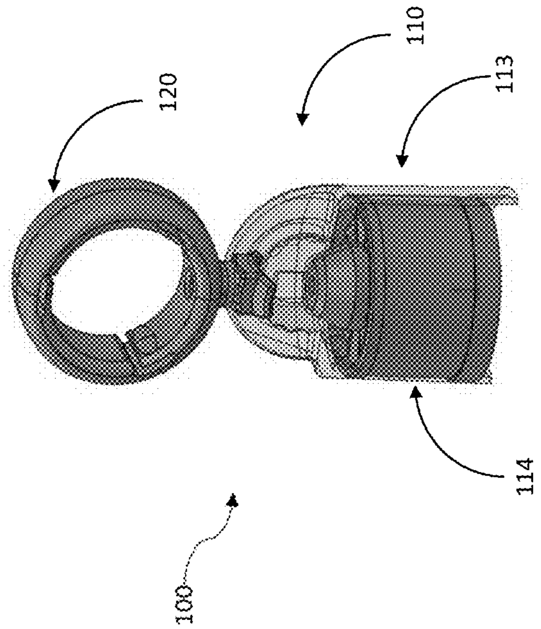
FIG. 6C is a transparent view of the outer shell of the adaptor, according to one embodiment.

FIG. 6C is a transparent view of the outer shell 113 of the adaptor 100, according to one embodiment of the present disclosure. The outer shell 113 can form a cavity surrounding the inner body 114. In one embodiment, the inner body 114 can rotate relative to the outer shell 113 while the outer shell 113 and/or the cosmetic holder 120 are fixed in place and do not rotate. For example, the inner body 114 can rotate in order to counteract an unintentional rotational movement of the motion stabilizer or the adaptor 100. The rotation of the inner body 114 is not translated to the cosmetic holder 120 because the cosmetic holder 120 is not in contact with the inner body 114. Similarly, the fitting of the outer shell 113 around the inner body 114 can include a gap between the outer shell 113 and the walls of the inner body 114 so that the rotation of the inner body 114 is not translated to the outer shell 113.

FIG. 6D is a transparent view of the inner body 114 of the adaptor 100, according to one embodiment of the present disclosure. The inner shell 114 can form the chamber 112, as has been described herein. The chamber 112 can extend to the top of the inner body. In one embodiment, the chamber 112 can be shaped as a central cylinder with two cylinders adjacent to the central cylinder, as illustrated in FIG. 6D. The shape of the chamber 112 and the symmetry of the chamber 112 can depend on the intended attachment to a motion stabilizer or other structure. In one embodiment, the shape of the chamber 112 can depend on the desired movement of the adaptor 100. For example, an infinitely symmetrical chamber can be attached onto a motion stabilizer in any orientation and can remain stationary when the motion stabilizer rotates. In another example, a chamber with limited axes of symmetry can result in a fixed number of orientations at which the adaptor can be attached to the motion stabilizer.

In one embodiment, the attachment of the cosmetic applicator to the motion stabilizer can activate at least one sensor to indicate that the adapter body 110 has been successfully attached to the motion stabilizer. The at least one sensor can be, for example, a Hall effect sensor that can detect and respond to the magnetic field produced by the adapter and/or the motion stabilizer. In one embodiment, the at least one sensor can be a pressure-activated sensor. Alternative sensors known to those of ordinary skill in the art can be compatible with the systems and apparatuses disclosed herein. In one embodiment, the at least one sensor can detect when the cosmetic applicator has not been attached to the motion stabilizer properly. For example, a Hall effect sensor can detect a partial magnetic field from the adapter with a magnitude that is less than an expected magnitude. The partial magnetic field can indicate that a portion of the ring-shaped magnet on the adapter is physically shielded or has failed to produce a magnetic field. In one embodiment, the data from the at least one sensor can be used to notify a user to inspect the cosmetic applicator or reattach the cosmetic applicator.

In one embodiment, the adapter 100 can include one or more sensors and/or an integrated circuit. The one or more sensors can include, but are not limited to, pressure sensors, light sensors, weight sensors, tension or force sensors, a Hall sensor, an accelerometer, a gyroscope, or the like. Data from the one or more sensors can be used to identify when a cosmetic has been inserted into or attached to the cosmetic applicator. In one embodiment, the data from the one or more sensors can be used to identify physical features of an attached cosmetic, such as a size, a shape, or a weight of the attached cosmetic. In one embodiment, the data from the one or more sensors can relate to a motion of the cosmetic applicator 100 or a motion of an attached component, such as the attached cosmetic or the motion stabilizer. In one embodiment, the data from the one or more sensors can be transmitted from the cosmetic applicator to a remote device, such as a server or a user device. In one embodiment, the cosmetic applicator can receive data, including instructions, from the same remote device or a second remote device. Further detail surrounding network In an embodiment, the system described above includes the functionality to auto-detect adapters to activate specific protocols to the motion stabilizer device 150. For instance, the motion stabilizer device 150 may perform auto detection of different adapters that are used for different cosmetics such as lipstick, mascara, etc. As soon as the adapter is connected to the handle of the motion stabilizer device 150, the handle will automatically recognize which style of adapter (for example, lipstick vs mascara) is attached and will load a specific set of protocols developed for that specific application.

In one embodiment, one or more motion stabilization components are placed in an internal sleeve, wherein the internal sleeve can be inserted into the motion stabilizer device 150. In one embodiment, the motion stabilizer device 150 comprises a hollow shell (e.g., cylindrical shell), and the internal sleeve containing motion stabilization components can be a cylindrical sleeve with a diameter that is smaller than the diameter of the motion stabilizer device 150. In an embodiment, the motion stabilization components are located in the internal sleeve. In an embodiment, the motion stabilization components are located in alignment with the positions illustrated in FIG. 3A and FIG. 3B.

In one embodiment, the internal sleeve forms a receptacle for one or more motion stabilization components. For example, in an embodiment, the internal sleeve forms cutouts along the length of the sleeve, the cutouts being sized for the one or more motion stabilization components. Each motion stabilization component can be placed or embedded in a cutout to be secured in the internal sleeve. In one embodiment, the internal sleeve can be a hollow cylinder, wherein motion stabilization components can be placed inside the hollow cylinder. The internal sleeve can enable placement of the motion stabilization components in the motion stabilizer device and removal of the motion stabilizer components from the motion stabilizer device as needed. In one embodiment, the cosmetic securement device can include a locking mechanism and/or an eject mechanism to secure and release the internal sleeve and the motion stabilizer components contained therein.

Figure 7A:
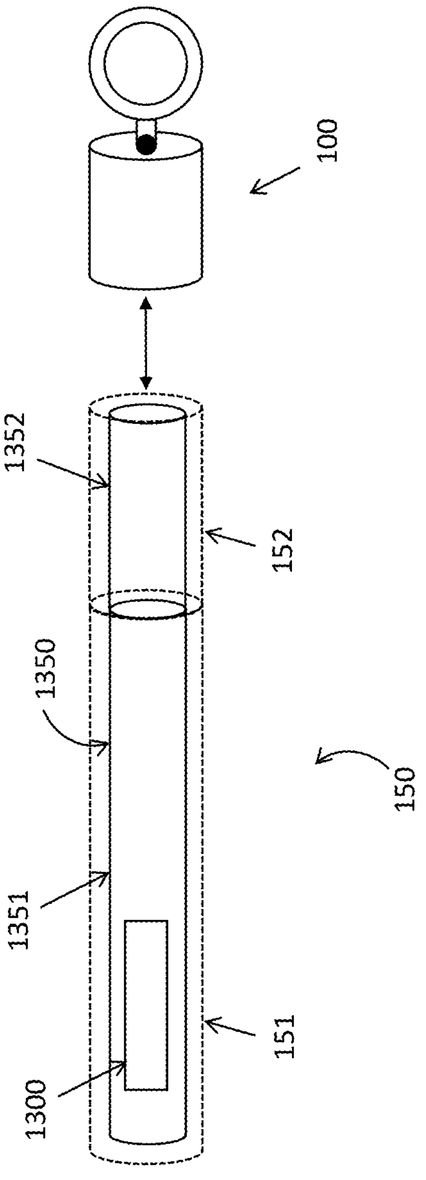
FIG. 7A shows an overview of a cosmetic securement device with an internal sleeve.

FIG. 7A is an illustration of an internal sleeve 1350 inside of a motion stabilizer device 150. In an embodiment, the internal sleeve 1350 fits inside the handle 151 and the receiver portion 152 of the motion stabilizer device 150. In one embodiment, the internal sleeve 1350 includes a handle sleeve 1351 and a receiver sleeve 1352, wherein the handle sleeve 1351 is aligned with the handle 151 of the motion stabilizer device 150 and the receiver sleeve 1352 is aligned with the receiver portion 152 of the motion stabilizer device 150 when the internal sleeve is inserted into the motion stabilizer device. The handle sleeve 1351 and the receiver sleeve 1352 can be removably attached to each other or can be formed as a single component. In one embodiment, the internal sleeve 1350 can include the receiver portion 152 of the motion stabilizer device. For example, the internal sleeve 1350 can include a receiver sleeve 1352 embedded inside the receiver portion 152. The internal sleeve 1350 can be inserted into the handle portion 151 such that the receiver portion 152, attached to the internal sleeve 1350, is coupled to the handle portion 151. The receiver sleeve 1352 can include components embedded inside the receiver portion 152. The cosmetic adapter 100 can be removably coupled to the motion stabilizer device 150 and/or the internal sleeve 1350 inserted into the motion stabilizer device.

In one embodiment, the internal sleeve 1350 can include any of the motion stabilization components illustrated in FIG. 3A and FIG. 3B. For example, the handle sleeve 1351 can include motion stabilization components such as the power source 1301, the printed circuit board assembly (PCBA) 1302, which may include positional sensor circuitry 1307, reader circuitry 1308, control circuitry 1309, and communication interface 1310. The receiver sleeve 1352 can include motion stabilization components such as the motive elements 1303, 1304, end effector coupling 1305 and RFID reader 1306, electromagnetic positioner 1311 including U-shaped magnetic cores 1312 arrayed around non-magnetic tube 1313, which is filled with a magnetic fluid 1314, and windings 1315 surrounding the magnetic cores. Any one or more of the motion stabilization components of FIG. 3A and FIG. 3B are illustrated schematically as motion stabilization component 1300 in FIG. 7A.

In one embodiment, the one or more motion stabilization components can be wired together within the internal sleeve 1350. For example, the power source 1301 can be electrically connected to the PCBA 1302, and the combination of the wired power source and PCBA can be placed in the internal sleeve. In one embodiment, the internal sleeve can include one or more electrical mating connectors for electrical connectivity between motion stabilization components. For example, the handle sleeve 1351 can include a PCBA 1302, wherein the PCBA 1302 is configured to transmit control data to motive elements 1303 and 1304 located in the receiver sleeve 1352. The handle sleeve 1351 and the receiver sleeve 1352 can each include electrical mating connectors and can be coupled together such that the PCBA 1302 in the handle sleeve 1351 can be electrically connected to the motive elements 1303, 1304 in the receiver 1352.

The internal sleeve 1350 can include different combinations of internal components, including motion stabilization components, in order to provide a modular cosmetic securement device for users with varying needs. For example, an internal sleeve can include control circuitry in a PCBA configured for data transmission to and from the cosmetic securement device but may not include motive elements. A user can be provided with a plurality of internal sleeves, wherein each sleeve can include different motion stabilization components embedded therein. The user can select an internal sleeve to insert into the motion stabilizer device based on their mobility or preferred operation of the motion stabilizer device. For example, a first internal sleeve can include a motive element configured for motion stabilization along one axis of movement and a second internal sleeve can include a plurality of motive elements configured for motion stabilization along a plurality of axes of movement. In one example, an internal sleeve 1350 can include motive elements configured for motion stabilization within a certain range of motion or displacement. Advantageously, the user only needs to handle the internal sleeve (e.g., inserting or removing the internal sleeve) to modify functionality of the cosmetic securement device rather than handling each motion stabilization component individually.

Figure 7B:
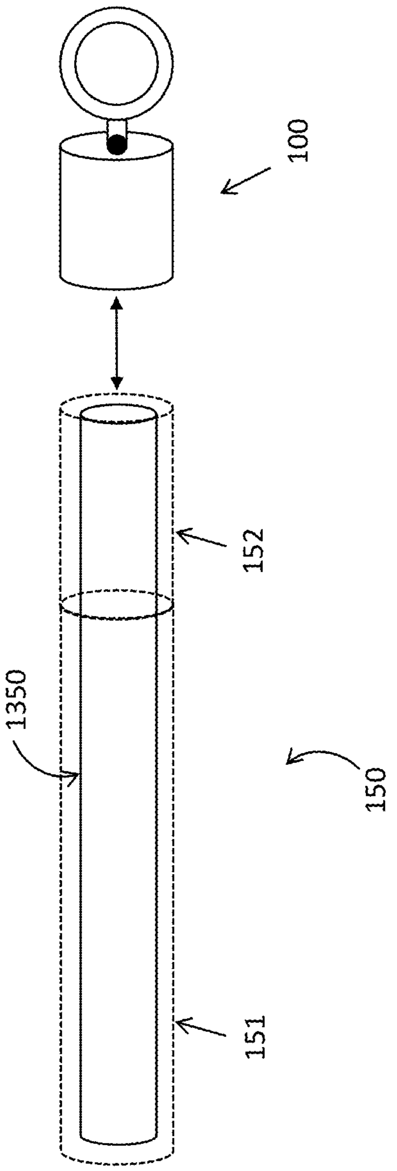
FIG. 7B shows an overview of a cosmetic securement device with a static internal sleeve.

In one embodiment, the internal sleeve 1350 can be a "static" sleeve, e.g., a sleeve that does not include motion stabilization components. In one such example, the internal sleeve 1350 can be a hollow or solid cylinder, such as a plastic cylinder without any motion stabilization components as illustrated in FIG. 7B. The internal sleeve 1350 can be a uniform, solid cylinder fitting inside the motion stabilizer device 150. The internal sleeve 1350 of FIG. 7B can be inserted into the motion stabilizer device as a physical core for the motion stabilizer device rather than for providing active motion stabilization or correction of any attached cosmetics. In one embodiment, the internal sleeve 1350 can be weighted, e.g., with a metal core. In one embodiment, a static sleeve can include electronic components, such as a PCBA, without motive elements that are configured for motion stabilization. It can be appreciated that any internal sleeves described and illustrated herein can include one or more motion stabilization components 1300 or can be static sleeves.

Figure 8A:
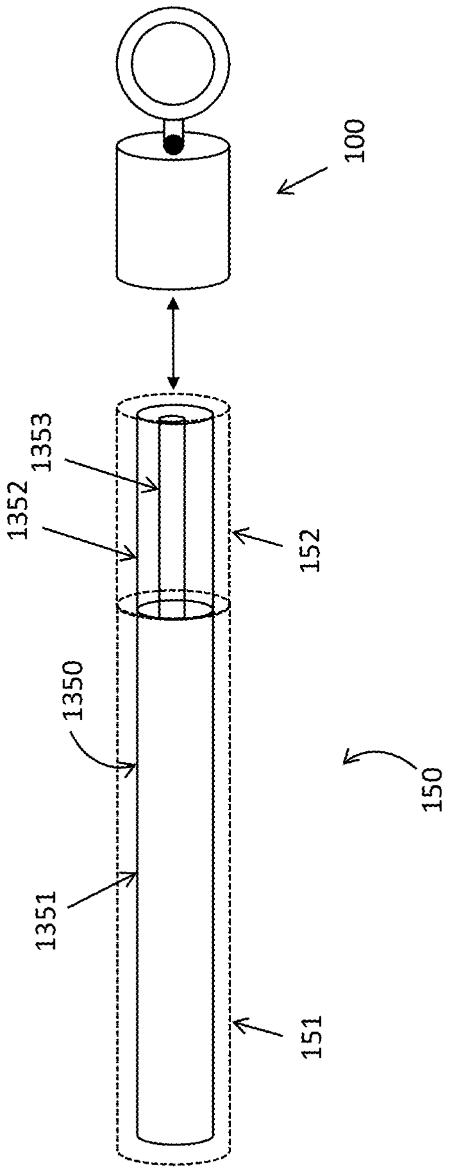
FIG. 8A shows an overview of a cosmetic securement device with a positioning joint in the internal sleeve.

In one embodiment, the internal sleeve can include one or more positioning joints, wherein the one or more positioning joints can be configured to hold an attached adapter 100 in a fixed position. The one or more positioning joints can be included in the receiver sleeve 1352 of the internal sleeve 1350. In one embodiment, a positioning joint can be a mechanical positioning joint. In one embodiment, a positioning joint can be a motorized positioning joint. FIG. 8A illustrates an example of an internal sleeve 1350 having a positioning joint 1353. The positioning joint 1353 of FIG. 8A can be a flexible joint in the receiver sleeve 1352. For example, the positioning joint 1353 can include a metal wire core. The positioning joint 1353 can be set, bent, folded, curved, kinked, etc. into a shape or position, e.g., at an angle, and can hold the position once set. In this manner, an adapter 100 attached to the receiver portion of the motion stabilizer can be held in a fixed position by the cosmetic securement device. In one embodiment, the receiver portion or receiver sleeve surrounding the positioning joint 1353 can be a flexible material, such as silicone, and can bend along with the positioning joint 1353.

Figure 8B:
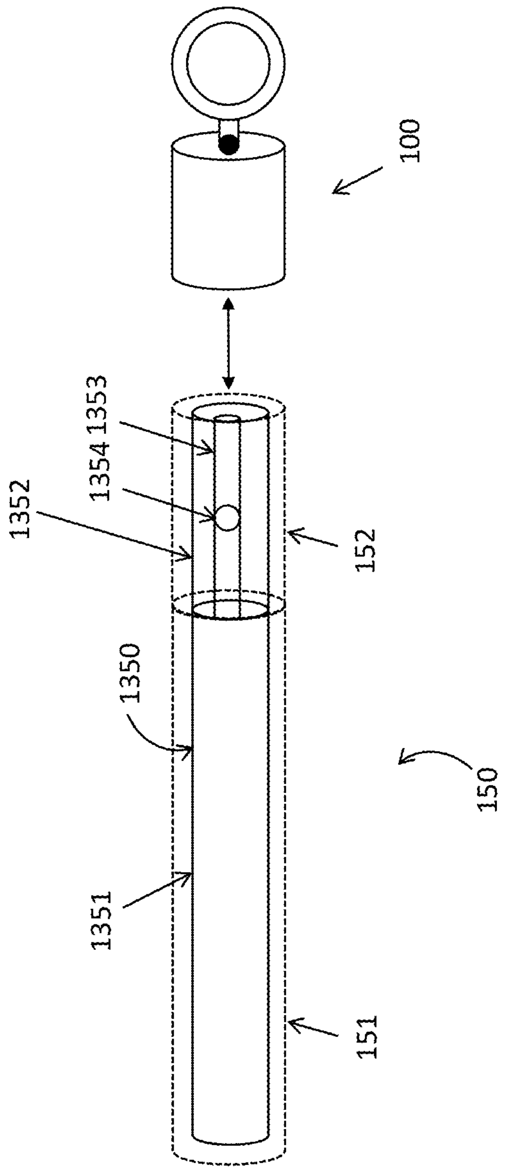
FIG. 8B shows an overview of a cosmetic securement device with a ball-joint positioning joint in the internal sleeve.
Figure 8C:
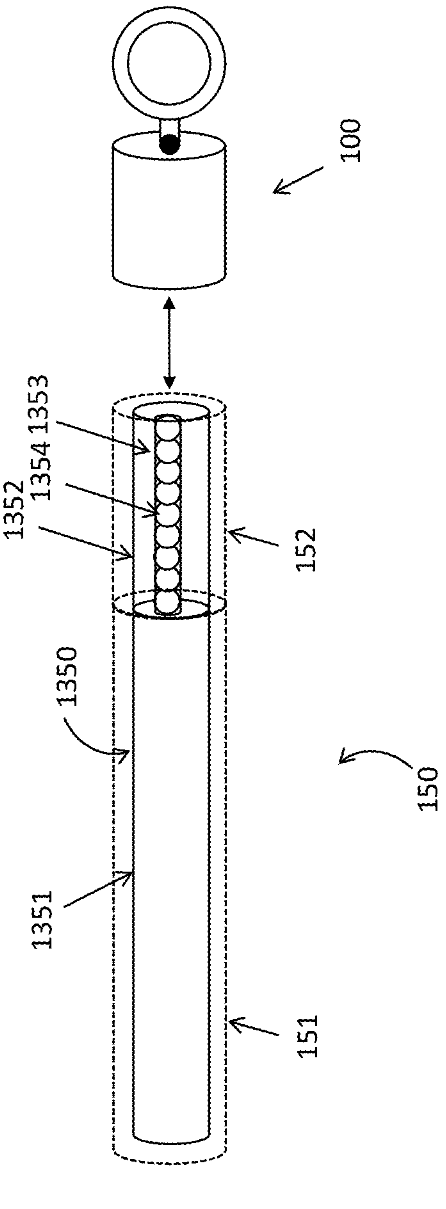
FIG. 8C shows an overview of a cosmetic securement device with a multi-joint positioning joint in the internal sleeve.

FIG. 8B illustrates an example of a positioning joint 1353 according to one embodiment, wherein the positioning joint 1353 is segmented by a ball joint 1354. The ball joint 1354 can provide a pivot point around which a portion of the positioning joint and surrounding receiver sleeve can be bent, rotated, or otherwise positioned. The ball joint 1354 can be configured for one or more degrees of freedom. It can be appreciated that a positioning joint 1353 can include any number of ball joints in order to provide higher precision in positioning. FIG. 8C illustrates an example of a multi-jointed positioning joint 1353 according to one embodiment, the positioning joint 1353 including a series of linked joints 1354. The connection point between each joint can provide a pivot point for bending and/or rotating a portion of the positioning joint 1353 and the receiver sleeve 1352.

The positioning joint 1353 in the internal sleeve can provide assistance for users who do not require active motion stabilization. For example, a user may have limited wrist mobility and may have difficulty holding a cosmetic product at a certain angle during application. However, the user may not experience tremors or unintentional movement. The user may therefore require a motion stabilizer device that can hold a cosmetic product at a set angle without any additional stabilization or assistance. The positioning joint 1353 can be conformed into a fixed position. Any tools or products attached to the adapter, such as a cosmetic tool held by the cosmetic holder, can also be fixed in a position that is based on the fixed position of the positioning joint 1353. The position of the positioning joint 1353 can be modified due to the flexibility (e.g., flexible material) of the positioning joint 1353. For example, when the user changes the cosmetic tool, the positioning joint 1353 can be adjusted to a different orientation or angle (different fixed position) based on the cosmetic tool.

In one embodiment, the positioning joint 1353 can be a motorized or automatic positioning joint. For example, the positioning joint 1353 of FIG. 8B can include an internal gear configured to rotate the ball joint 1354. The rotation of the ball joint by the internal gear can be based on an electrical signal to the internal gear. In this manner, a user can control the position of the positioning joint 1353 remotely. In one embodiment, the motion stabilizer device 150 can include a switch or button along the external wall of the motion stabilizer device 150. Activation (e.g., pressing) of the switch or button can result in the internal gear being turned, thus resulting in rotation of the ball joint.

Figure 9A:
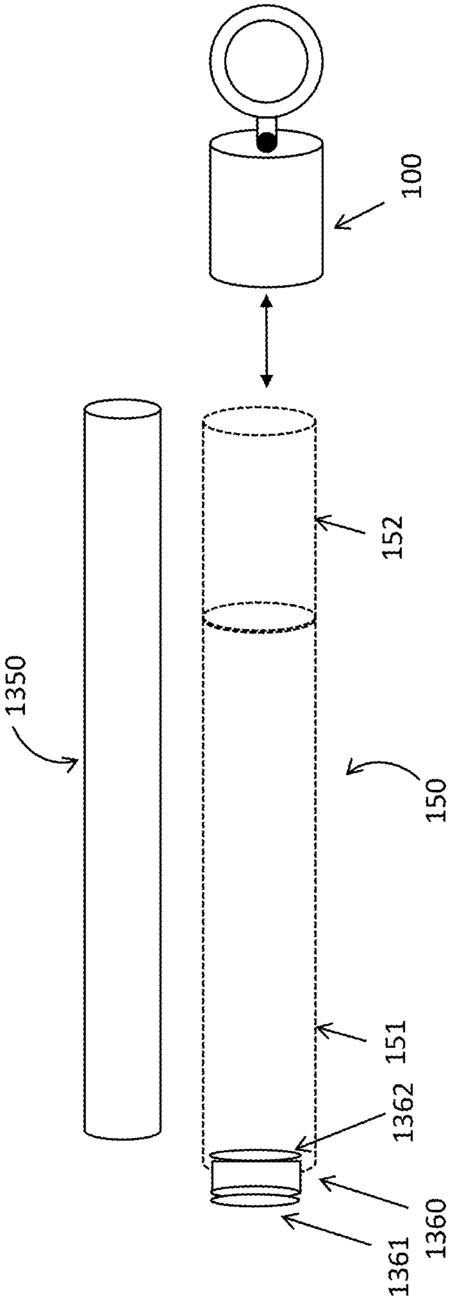
FIG. 9A shows an overview of a cosmetic securement device with a locking mechanism.
Figure 9B:
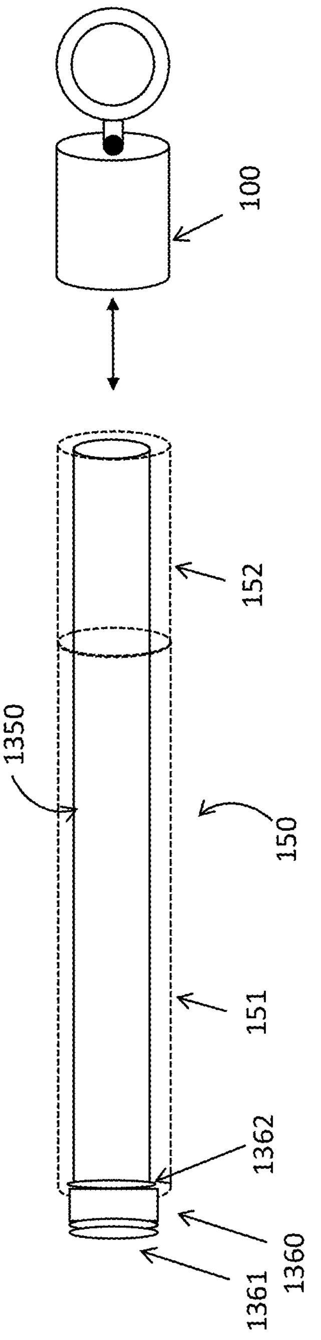
FIG. 9B shows an overview of a cosmetic securement device with a locking mechanism.

In one embodiment, the motion stabilizer device 150 and/or the internal sleeve 1350 can include locking mechanisms, such as latches, joints, connectors, attachments, etc. in order to secure the internal sleeve 1350 inside of the motion stabilizer device 150. FIG. 9A illustrates an example of a locking mechanism including a button 1360 at the base of the handle 151. In one embodiment, the button 1360 can be a push button latch, wherein the button 1360 can be depressed in order to engage or disengage the latching (locking) of the internal sleeve 1350 to the inner wall of the handle 151. The knob 1361 of the button can be exposed at the base of the handle 151. The knob 1361 can refer to a depressible portion of the button that can be pushed or pulled to engage the latching of the internal sleeve inside the handle. The body 1362 of the button 1360 can be provided inside of the handle. FIG. 9B is an illustration of the internal sleeve 1350 inserted into the motion stabilizer device 150. In one embodiment, the base of the internal sleeve 1350 can be in contact with the body 1362 of the button in order to secure the internal sleeve 1350 inside the handle. In one embodiment, the base of the internal sleeve 1350 can fit into the body of the button. For example, the body 1362 of the button can form a ring, wherein the base of the internal sleeve can fit inside the ring. In one embodiment, the body 1362 of the button can form a snap-fit joint, wherein the insertion force of the internal sleeve can deform the body 1362 of the button to widen and fit around the base of the internal sleeve. When the internal sleeve is inserted, the body 1362 of the button can secure the base of the internal sleeve such that the internal sleeve is not displaced by movement of the motion stabilizer device.

In one embodiment, the knob 1361 of the button 1360 can be used to disengage the internal sleeve from the body 1362 of the button. For example, pushing the knob 1361 can cause the body 1362 of the button to deform (widen) so that the internal sleeve is released from the snap fit joint formed with the body 1362 of the button. In one embodiment, the base of the internal sleeve can be in contact with the body 1362 of the button. A pushing force applied to the button can be transferred to the internal sleeve. Pushing the knob 1361 can cause a displacement of the body 1362 of the button and the internal sleeve towards the receiver portion 152. The applied force and displacement of the internal sleeve can release the internal sleeve from a locking mechanism. The position of the knob 1361 at the base of the handle can be advantageous in that a user can easily push the knob without small or precise movements. In one use case, the knob 1361 can be engaged by pushing the base of the handle against any surface, such as a table. The internal sleeve can then be removed from the handle of the motion stabilizer device.

Figure 10A:
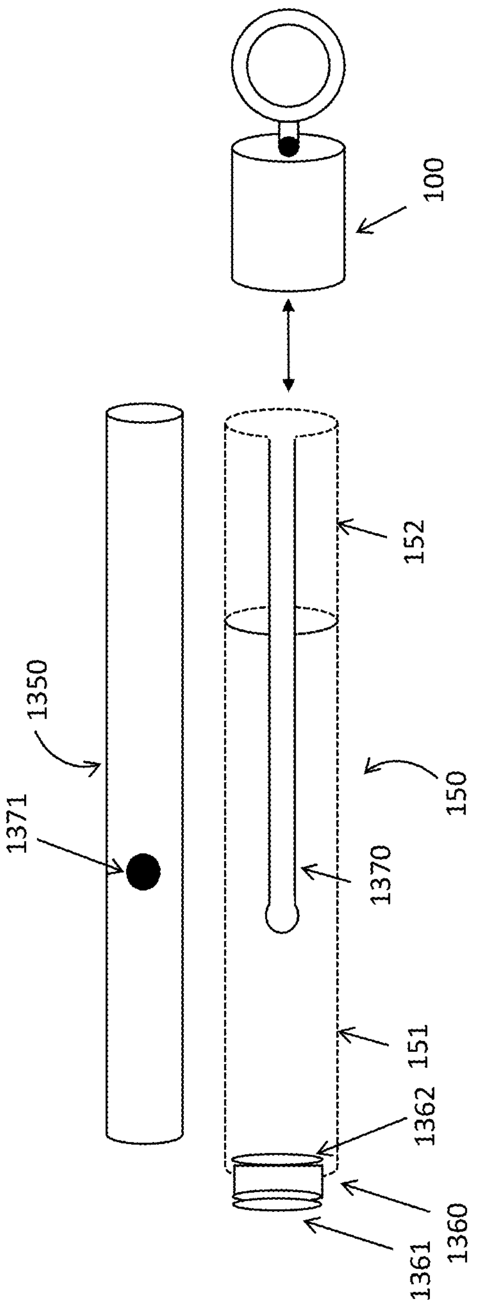
FIG. 10A shows an overview of a cosmetic securement device with a locking mechanism along the outer wall of the motion stabilizing device.
Figure 10B:
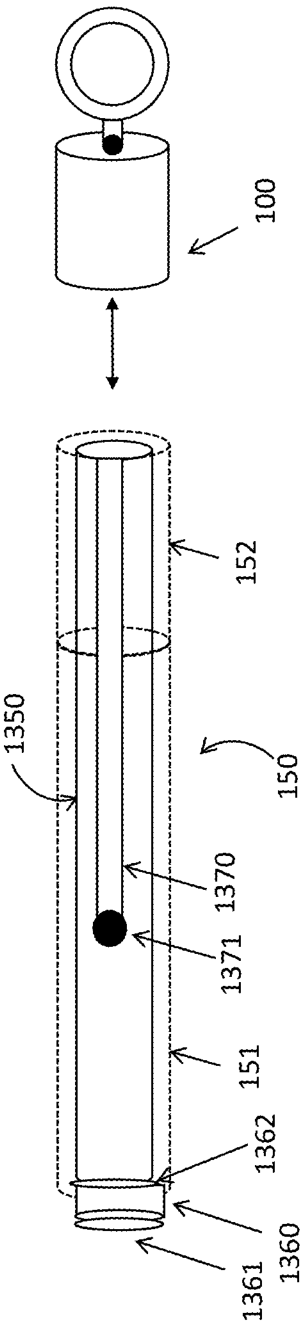
FIG. 10B shows an overview of a cosmetic securement device with a locking mechanism along the outer wall of the motion stabilizing device.

FIG. 10A is an illustration of a locking mechanism according to one embodiment of the present disclosure. The side wall of the handle 151 and the receiver portion 152 can form a groove or cutout 1370 running along a portion of the length of handle portion 151 and/or receiver portion 152. The cutout 1370 can run along the outer wall or the inner wall of the handle portion 151 and/or receiver portion 152. The outer wall of the internal sleeve 1350 can form a projection 1371, wherein the projection 1371 can fit in the cutout 1370 when the internal sleeve 1350 is inserted into the motion stabilizer device. FIG. 10B is an illustration of the internal sleeve 1350 inserted in the motion stabilizer device 150 wherein the projection 1371 fits into the cutout 1370. In one embodiment, the base of the cutout 1370 can form a snap-fit joint, wherein the projection 1371 can fit into the base of the cutout 1370 such that the internal sleeve 1350 is secured inside the handle 151. The button 1360 at the base of the handle 151 can be used to release the internal sleeve 1350. For example, pushing (depressing) the knob 1361 of the button 1360 can result in displacement of the body 1362 of the button towards the receiver portion 152. The body of the button can apply a pushing force to the internal sleeve 1350, wherein the pushing force can disengage the projection 1371 from the base of the cutout 1370. The internal sleeve 1350 can then be removed from the handle 151. In one embodiment, the side wall of the handle 151 can include a plurality of parallel cutouts running along a portion of the length of the handle 151. As a result, the internal sleeve 1350 can be inserted in more than one orientation, thereby reducing the precision of motion required from the user in order to insert and lock the internal sleeve.

Figure 11A:
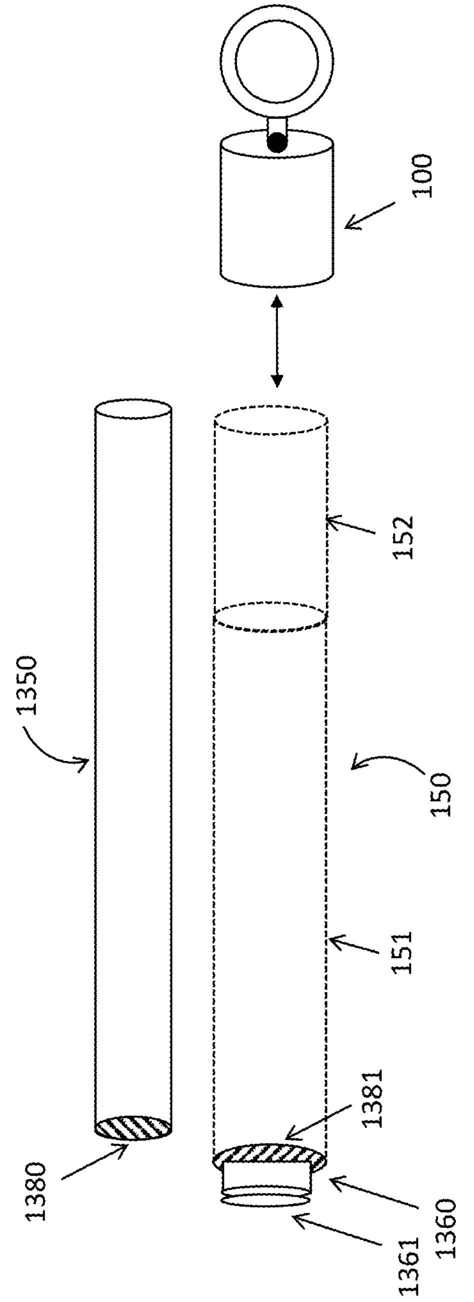
FIG. 11A shows an overview of a cosmetic securement device with a magnetic locking mechanism.
Figure 11B:
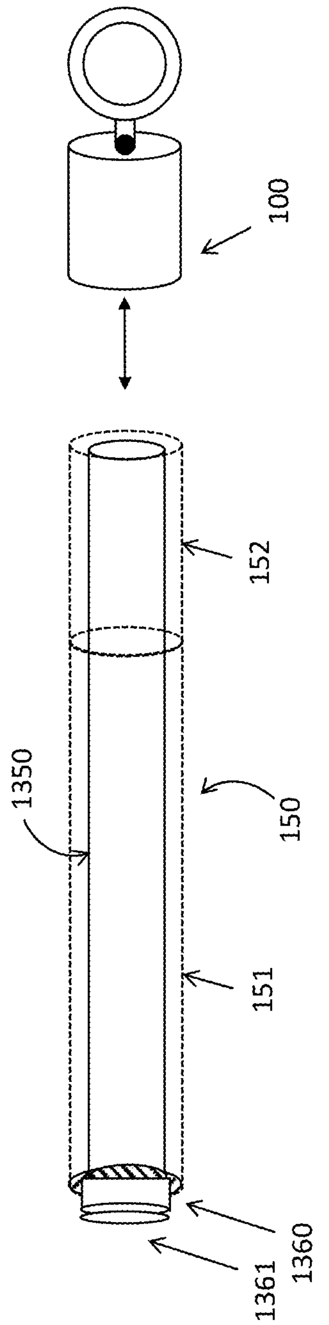
FIG. 11B shows an overview of a cosmetic securement device with a magnetic locking mechanism.

In one embodiment, the locking mechanism can include a magnetic attachment. For example, a portion 1380 of the outer surface of the internal sleeve 1350 (e.g., the base of the internal sleeve) and a portion 1381 of the inner surface of the handle 151 (e.g., the inner surface of the bottom face) can be magnetized, as illustrated in FIG. 11A. When the internal sleeve 1350 is inserted into the handle 151, the magnetic force between the magnetized portions 1380 and 1381 can secure the internal sleeve 1350 to the handle 151, as illustrated in FIG. 11B. In one embodiment, the button 1360 at the base of the handle 151 can be used to release the internal sleeve 1350. For example, pushing (depressing) the knob 1361 of the button 1360 can displace the internal sleeve 1350 so that one end of the internal sleeve 1350 emerges from the receiver portion 152. The internal sleeve 1350 can then be handled and removed. The magnetized portions 1380 and 1381 illustrated in FIG. 11A and FIG. 11B are presented as non-limiting examples. Additional or alternative portions of the internal sleeve and the handle can be magnetized to provide a magnetic attachment between the internal sleeve and the handle.

Figure 12A:
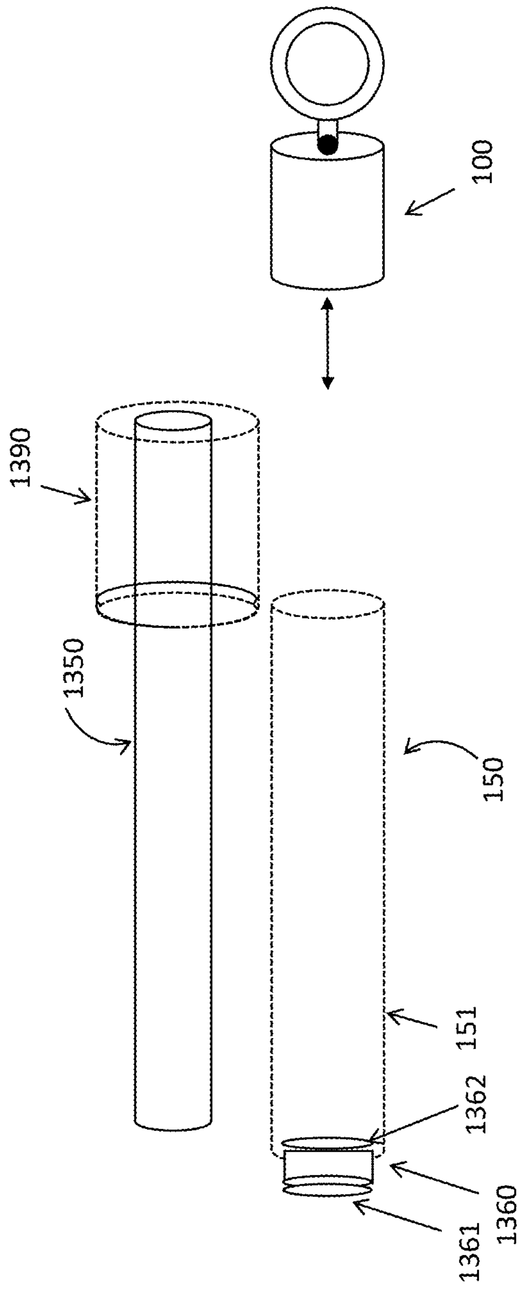
FIG. 12A shows an overview of a cosmetic securement device wherein the internal sleeve includes a cap.
Figure 12B:
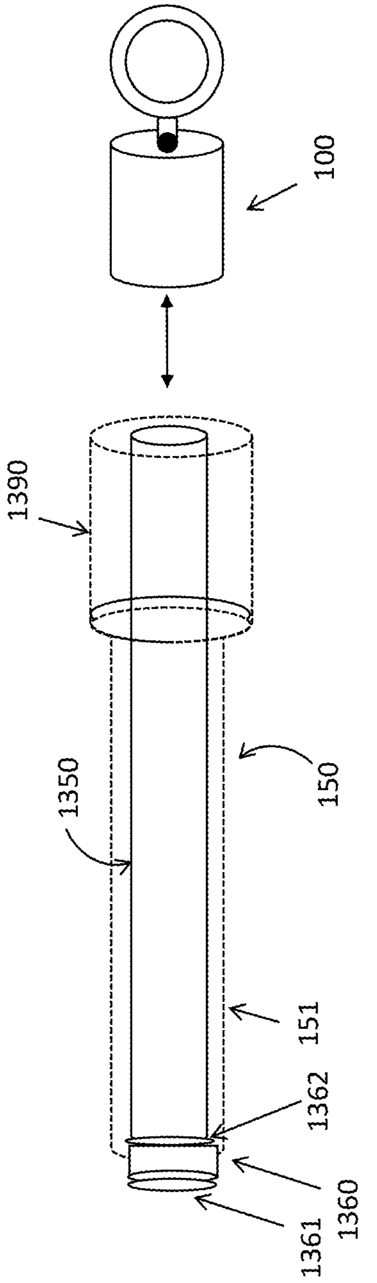
FIG. 12B shows an overview of a cosmetic securement device wherein the internal sleeve includes a cap.

FIG. 12A is an illustration of a locking mechanism according to one embodiment of the present disclosure. The internal sleeve 1350 can form a cap 1390 around the receiver sleeve 1352. The cap 1390 can be a cylindrical shell surrounding the receiver sleeve of the internal sleeve 1350, as illustrated in FIG. 12A. In one embodiment, the cap 1390 can be a tapered shell, such as an approximately conical shape. In one embodiment, the cap 1390 can form the receiver portion of the motion stabilizer device. For example, the cap 1390 can surround the receiver sleeve 1352 and can be coupled to the handle portion 151 of the motion stabilizer device 150. In one example, the cap 1390 can be wider than the handle portion 151 and can fit over or around the handle portion 151 when the internal sleeve 1350 is inserted into the motion stabilizer device 150, as illustrated in FIG. 12B. The dimensions of the cap 1390 and the handle portion 151 can be configured so that the cap 1390 forms a tight fit over the handle portion 151 in order to secure the inner sleeve 1350 inside the handle portion 151. The button 1360 at the base of the handle 151 can be used to release the internal sleeve 1350 by applying a pushing force to the internal sleeve 1350 to displace the internal sleeve 1350 outwards from the handle 151.

Figure 13A:
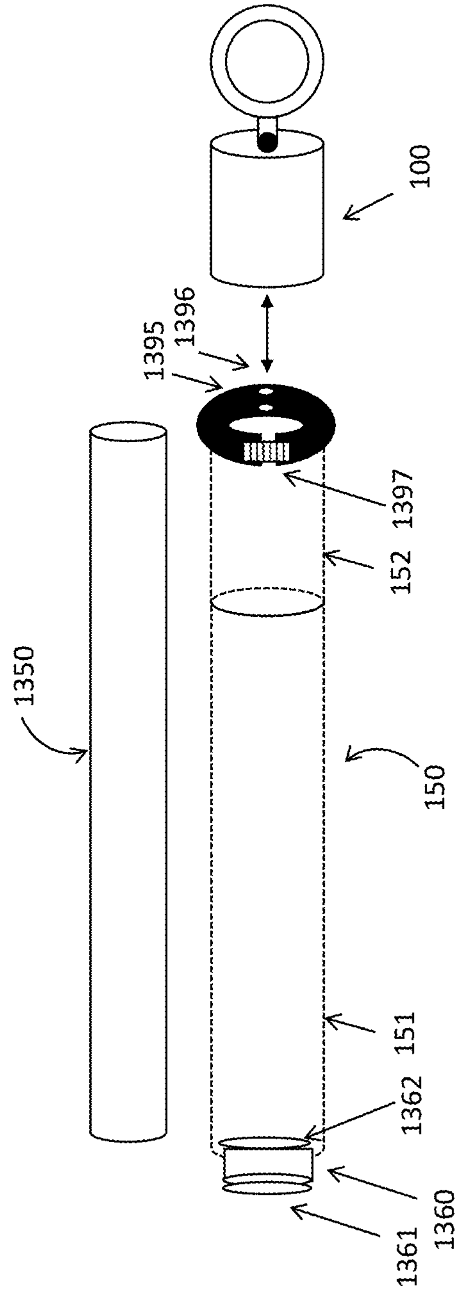
FIG. 13A shows an overview of a cosmetic securement device with a latch locking mechanism.
Figure 13B:
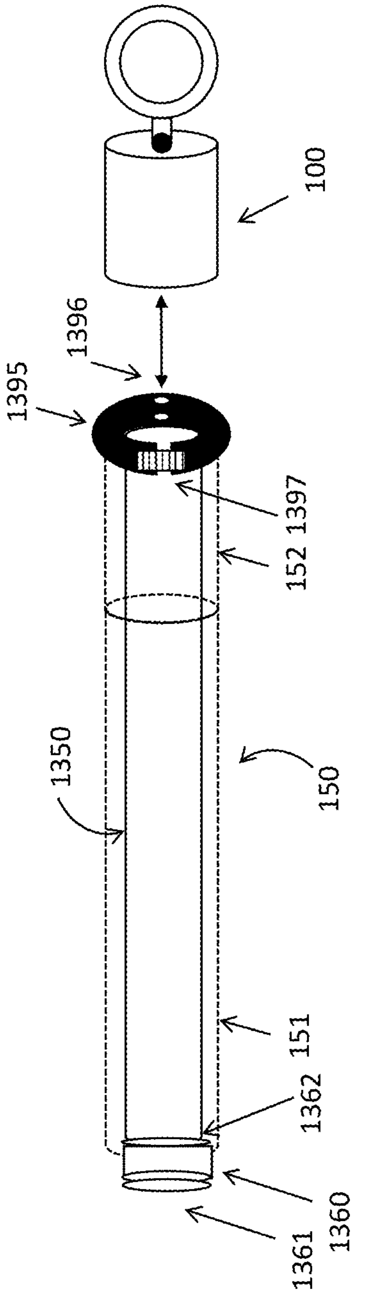
FIG. 13B shows an overview of a cosmetic securement device with a latch locking mechanism.

In one embodiment, the locking mechanism can be located on the outer surface of the motion stabilizer device, as illustrated in FIG. 13A. For example, the receiver portion 152 of the motion stabilizer device can include a collar 1395 at the opening of the receiver portion 152 where the internal sleeve is inserted. In one embodiment, the collar 1395 can be formed by two halves, wherein the two halves can be attached via a hinge 1396 at one end. The two halves can rotate around an axis formed by the hinge 1396. The two halves can be rotated into an open position, e.g., wherein the two halves are not both in contact with the edge of the receiver portion 152, and a closed position, e.g., wherein the two halves are in contact with the edge of the receiver portion 152. In one embodiment, the two halves can be coupled together in the closed position by a latch 1397. The collar 1395 can extend radially inwards such that the collar 1395 is in contact with the outer wall of the internal sleeve 1350 when the internal sleeve 1350 is inserted into the motion stabilizer device and the collar 1395 is in a closed position. FIG. 13B illustrates the collar 1395 secured in the closed position around the internal sleeve by closing the latch 1397. In one embodiment, the latch 1397 can be opened to move the two halves of the collar 1395 into an open position and release and remove the internal sleeve 1350 from the receiver portion 152. In one embodiment, the latch 1397 can be released via a button or switch. A button or similar push mechanism may be easier to press for a user with limited mobility.

It can be appreciated that the locking mechanisms illustrated herein are presented as non-limiting embodiments that can be combined or altered in order to secure the internal sleeve 1350 in the motion stabilizer device 150. For example, in some embodiments, the button 1360 can be a slider, a switch, a wheel (e.g., a clickwheel), etc. In one embodiment, the button 1360 can be attached to a gear, wherein engaging the button can result in rotation of the gear to apply a force to the internal sleeve to lock or release the internal sleeve. In one embodiment, the button 1360 can be located along the side of the handle portion 151 or the receiver portion 152. In one embodiment, the button 1360 can be located on the internal sleeve 1350. For example, the button 1360 can be located at the base of the internal sleeve 1350. The base of the handle portion 151 can form a ring such that the base of the internal sleeve 1350 is exposed when the internal sleeve 1350 is inserted into the motion stabilizer device.

The modularity of the internal sleeve 1350 can enable usage of different handle portions of the cosmetic securement device. The shape and size of the handle portion 151, as well as ergonomic features, can vary based on user needs. For example, a handle portion 151 with different dimensions or a non-cylindrical shape (e.g., a tapered handle portion with a wider base) may be preferable for certain users. In one example, a handle portion 151 with grip enhancements, such as a textured exterior surface or a strap, may be preferable for certain users. The internal sleeve 1350 containing any motion stabilization components can be easily removed from a first handle portion having a first design and inserted into a second handle portion having a second design. In this manner, each handle can be provided with motion stabilization components contained in the internal sleeve 1350. Similarly, if motion stabilization is not desired, each handle can be provided with a static internal sleeve. Motion stabilization needs for a single user can vary over time due to a number of factors, such as symptom flare-ups, treatment plans, medication, overall health, time of day, diet, etc. Thus, it can be helpful for a single user to be able to swap out a number of internal motion stabilization components with a number of handles for improved comfort and usability.

In one embodiment, an indication for usage of an internal sleeve 1350 can be provided by an automated diagnosis application. In one embodiment, the methods of the automated diagnosis application described herein can be performed by one or more computing devices, e.g., a mobile device, a computer, a server, etc. The one or more computing devices can be accessed via a communication network by other computing devices or by the cosmetic securement device. In one embodiment, the one or more computing devices can be accessed via a mobile application or a web-based application. In one embodiment, the automated diagnosis application can be executed by, or can be in communication with, the cosmetic securement device of the present disclosure. In one embodiment, the one or more computing devices can be configured to determine whether a user should use a static internal sleeve (e.g., without motive elements) or a dynamic internal sleeve (e.g., with motive elements). In one embodiment, the one or more computing devices can receive sensor data from the motion stabilizer device, such as movement data collected by the at least one inertial sensor and the at least one distributed motion sensor. The movement data can indicate the movement and orientation of the motion stabilizer device. The circuitry of the motion stabilizer device can be configured to collect and transmit the movement data to the one or more computing devices. In one embodiment, the one or more computing devices can receive user data, such as information about a user's diagnosis, condition, routine, etc. The one or more computing devices can determine whether motion stabilization is necessary for the user based on the received data. For example, the one or more computing devices can receive movement data indicating small, erratic movement of the motion stabilizer device due to a user's tremors. The one or more computing devices can determine via the automatic diagnosis application that motion stabilization is necessary in order for the user to continue using the motion stabilizer device. In one example, the one or more computing devices can determine that a type of motion stabilization (e.g., tremor correction) is necessary, wherein the type of motion stabilization can correspond to an internal sleeve containing a combination of motion stabilization components. In one embodiment, the one or more computing devices can transmit data to another computing device and/or to the cosmetic securement device. For example, the one or more computing devices can transmit diagnosis data indicating motion stabilization components in an internal sleeve that the user should use. In one example, the diagnosis data can be transmitted to the cosmetic securement device. The cosmetic securement device can include an indicator, such as one or more light-emitting diodes (LEDs). The cosmetic securement device can control the current through the one or more light-emitting diodes based on the received diagnosis data in order to indicate an internal sleeve to be used.

Obviously, numerous modifications and variations of the present invention are possible in light of the above teachings. It is therefore to be understood that within the scope of the appended claims, the invention may be practiced otherwise than as specifically described herein.

The invention claimed is:

1. A cosmetic securement device for stabilization of a cosmetic applicator, comprising:

a motion stabilizer handle with a proximal end and a distal end;

an internal sleeve configured to be removably inserted into the distal end of the motion stabilizer handle until positioned at the proximal end of the motion stabilizer handle;

an adapter coupled to a distal end of the internal sleeve; and a motion generation device configured to control a motion of the adapter according to a determined compensation movement, wherein the internal sleeve includes at least one positioning joint at the distal end of the internal sleeve, the distal end of the internal sleeve aligning with a distal end of the motion stabilizer handle when the internal sleeve is inserted into the motion stabilizer handle, wherein the motion stabilizer handle includes at least one releasable locking mechanism configured to secure the internal sleeve inside the motion stabilizer handle, and wherein the adapter is configured to hold a plurality of different types of cosmetic applicators.

2. The device according to claim 1, wherein the at least one releasable locking mechanism includes a snap-fit joint formed by the internal sleeve and the motion stabilizer handle.

3. The device according to claim 1, wherein the motion stabilizer handle includes a button and wherein depressing the button releases the internal sleeve from the at least one releasable locking mechanism.

4. The device according to claim 3, wherein the button is provided at the proximal end of the motion stabilizer handle.

5. The device according to claim 1, wherein the at least one positioning joint comprises one or more of a flexible metal wire core or a ball joint.

6. The device according to claim 1, wherein the adapter is coupled to the at least one positioning joint when the internal sleeve is inserted into the motion stabilizer handle.

7. A cosmetic securement device for stabilization of a cosmetic applicator, comprising:

a motion stabilizer handle with a proximal end and a distal end;

an internal sleeve configured to be removably inserted into the distal end of the motion stabilizer handle until positioned at the proximal end of the motion stabilizer handle;

an adapter coupled to a distal end of the internal sleeve;

wherein the internal sleeve includes at least one positioning joint at the distal end of the internal sleeve, the distal end of the internal sleeve aligning with the distal end of the motion stabilizer handle when the internal sleeve is inserted into the motion stabilizer handle, wherein the internal sleeve includes at least one sensor configured to detect movement caused by a user; and a motion generation device to control a motion of the adapter based on the detected movement caused by the user, wherein the motion stabilizer handle includes at least one releasable locking mechanism configured to secure the internal sleeve inside the motion stabilizer handle, and wherein the adapter is configured to hold a plurality of different types of cosmetic applicators.

8. The device according to claim 7, wherein the at least one sensor includes an inertial sensor and a distributed motion sensor, and wherein the movement data includes an orientation and an acceleration of the motion stabilizer handle.

9. The device according to claim 7, wherein the at least one releasable locking mechanism includes a snap-fit joint formed by the internal sleeve and the motion stabilizer handle.

10. The device according to claim 7, wherein the motion stabilizer handle includes a button and wherein depressing the button releases the internal sleeve from the at least one releasable locking mechanism.

11. The device according to claim 7, wherein the at least one positioning joint includes a flexible wire core.

12. The device according to claim 7, wherein the adapter is coupled to the at least one positioning joint when the internal sleeve is inserted into the motion stabilizer handle.

13. A cosmetic securement device for stabilization of a cosmetic applicator, comprising:

a motion stabilizer handle with a proximal end and a distal end;

an internal sleeve configured to be removably inserted into the distal end of the motion stabilizer handle until positioned at the proximal end of the motion stabilizer handle; and an adapter coupled to the distal end of the internal sleeve, wherein the internal sleeve includes at least one sensor configured to detect movement caused by a user, circuitry configured to determine a compensation movement to offset the detected movement, and at least one motion generation device embedded in the distal end of the internal sleeve configured to control a motion of the adapter according to the determined compensation movement, wherein the distal end of the internal sleeve aligns with the distal end of the motion stabilizer handle when the internal sleeve is inserted into the motion stabilizer handle, wherein the motion stabilizer handle includes at least one releasable locking mechanism configured to secure the internal sleeve inside the motion stabilizer handle, and wherein the adapter is configured to hold a plurality of different types of cosmetic applicators.

14. The device according to claim 13, wherein the at least one sensor includes an inertial sensor and a distributed motion sensor.

15. The device according to claim 13, wherein the at least one releasable locking mechanism includes a snap-fit joint formed by the internal sleeve and the motion stabilizer handle.

16. The device according to claim 13, wherein the motion stabilizer handle includes a button and wherein depressing the button releases the internal sleeve from the at least one releasable locking mechanism, and wherein the button is provided at the proximal end of the motion stabilizer handle.

17. The device according to claim 13, wherein the adapter is coupled to the motion generation device when the internal sleeve is inserted into the motion stabilizer handle.

18. The system according to claim 13, wherein the internal sleeve includes one or more positioning joints positioned within and at the distal end of the internal sleeve, and wherein the positioning joint comprises an adjustable flexible material configured to be positioned to one or more fixed positions.

19. The system according to claim 13, wherein the positioning joint comprises an automatic positioning joint including an internal gear configured to rotate a ball joint of the automatic positioning joint via electrical signals from a controller positioned within the cosmetic securement device.

* * * * *